(12) United States Patent
Gurd et al.

(10) Patent No.: US 9,161,965 B2
(45) Date of Patent: Oct. 20, 2015

(54) TREATMENT FOR EPILEPSY

(75) Inventors: James Gurd, Toronto (CA); Crystal Dykstra, Toronto (CA); Michael Tymianski, Toronto (CA)

(73) Assignee: NoNO Inc. (CA)

( * ) Notice: Subject to any disclaimer, the term of this patent is extended or adjusted under 35 U.S.C. 154(b) by 737 days.

(21) Appl. No.: 12/466,208

(22) Filed: May 14, 2009

(65) Prior Publication Data

US 2010/0160240 A1 Jun. 24, 2010

Related U.S. Application Data

(60) Provisional application No. 61/054,109, filed on May 16, 2008.

(51) Int. Cl.
| A61K 38/08 | (2006.01) |
| A61K 31/196 | (2006.01) |
| A61P 25/08 | (2006.01) |
| A61K 38/17 | (2006.01) |
| A61K 45/06 | (2006.01) |

(52) U.S. Cl.
CPC ............. A61K 38/1787 (2013.01); A61K 45/06 (2013.01); C07K 2319/10 (2013.01)

(58) Field of Classification Search
CPC . A61K 45/06; A61K 38/1787; C07K 2319/10
USPC .................................................. 514/1.1, 563
See application file for complete search history.

(56) References Cited

U.S. PATENT DOCUMENTS

| 7,595,297 | B2 * | 9/2009 | Tymianski ....................... 514/1.1 |
| 2003/0050243 | A1 * | 3/2003 | Tymianski ....................... 514/12 |
| 2005/0019841 | A1 | 1/2005 | Garman et al. |
| 2005/0282743 | A1 | 12/2005 | Lu et al. |
| 2006/0148711 | A1 * | 7/2006 | Lu et al. ........................... 514/13 |
| 2007/0021501 | A1 * | 1/2007 | Twyman et al. ............... 514/483 |
| 2008/0119412 | A1 | 5/2008 | Tymianski et al. |
| 2008/0274977 | A1 * | 11/2008 | Belmares et al. ................ 514/13 |
| 2009/0036376 | A1 | 2/2009 | Tasker et al. |
| 2009/0062213 | A1 | 3/2009 | Belmares et al. |
| 2009/0075377 | A1 | 3/2009 | Lu et al. |
| 2009/0176713 | A1 | 7/2009 | Tymianski et al. |
| 2010/0062985 | A1 | 3/2010 | Belmares et al. |
| 2010/0160240 | A1 | 6/2010 | Gurd et al. |

FOREIGN PATENT DOCUMENTS

| EP | 1 884 521 A1 | 2/2008 |
| WO | WO 2007079406 A1 * | 7/2007 |

OTHER PUBLICATIONS

PCT Search Report for application PCT/US2009/43831 mailed Aug. 5, 2009.
PCT Written Opinion of the International Searching Authority for application PCT/US2009/43831 mailed Aug. 5, 2009.
Cui, et al., "PDZ Protein Interactions Underlying NMDA Receptor-Mediated Excitotoxicity and Neuroprotection by PSD-95 Inhibitors" *Journal of Neuroscience*, 27(37):9901-9915 Sep. 12, 2007.
European Supplemental Search Report for EP09747499.3 dated Mar. 14, 2012.
Holsti, et al., "Prehospital Intranasal Midazolam for the Treatment of Pediatric Seizures" *Pediatric Emergency Care* vol. 23, No. 3:148153 ( Mar. 2007).
Jin, et al., "Electro-acupuncture improves epileptic seizures induced by kainic acid in taurine-depletion rats," *Acupunct Electrother Res*, 30(3-4):207-217 (2005) Abstract only.
Piserchio, et al., "Targeting Specific PDZ Doomains of PSD-95: Structural Basis for Enhanced Affinity and Enzymatic Stability of a Cyclic Peptide" *Chemistry & Biology*, vol. 11:469-473 (Apr. 2004).
Saransaari, et al., "Phencylidine-binding sites in mouse cerebral cortex during development and ageing: effects of inhibitory amino acids," *Mech Ageing Dev.*, 68(1-3):125-136 (May 1993) Abstract only.
Zeng, et al., "The Mammalian Target of Rapamycin (mTOR) Signaling Pathway Mediates Epileptogenesis in a Model of Temporal Lobe Epilepsy", *J. Neurosci* , 29(21):6964-6972 (May 27, 2009).

\* cited by examiner

*Primary Examiner* — Gregory S Emch
(74) *Attorney, Agent, or Firm* — Alston & Bird LLP

(57) ABSTRACT

The invention provides methods of treating a patient having epilepsy in which an effective regime of an agent that inhibits specific binding of PSD-95 to an NMDA receptor is administered to a patient.

13 Claims, 15 Drawing Sheets

Figure 1
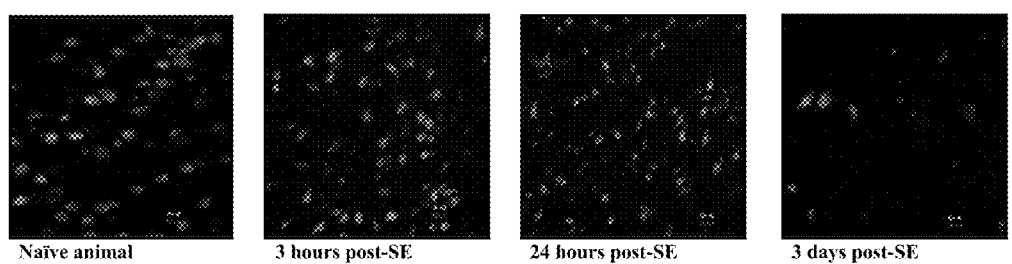
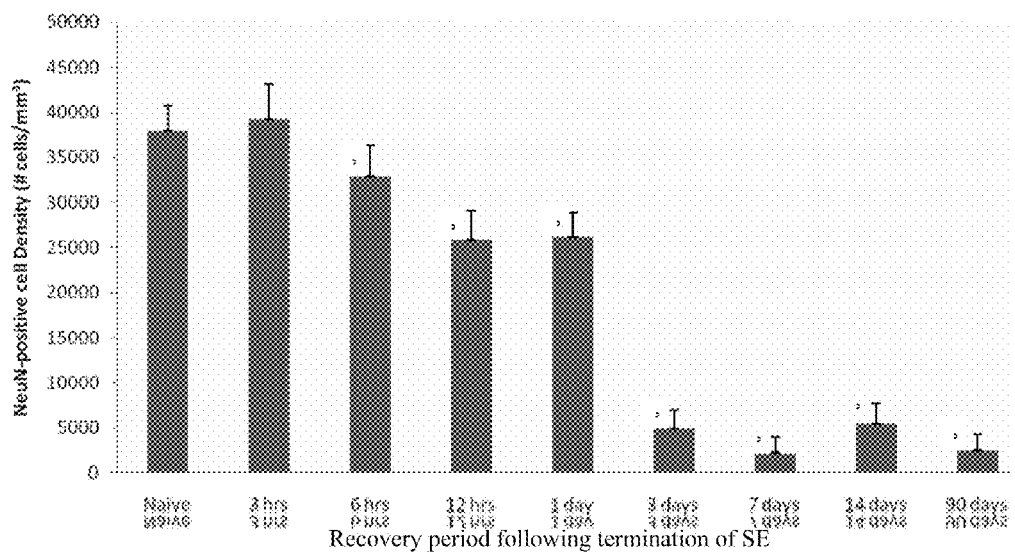

Figure 2
A
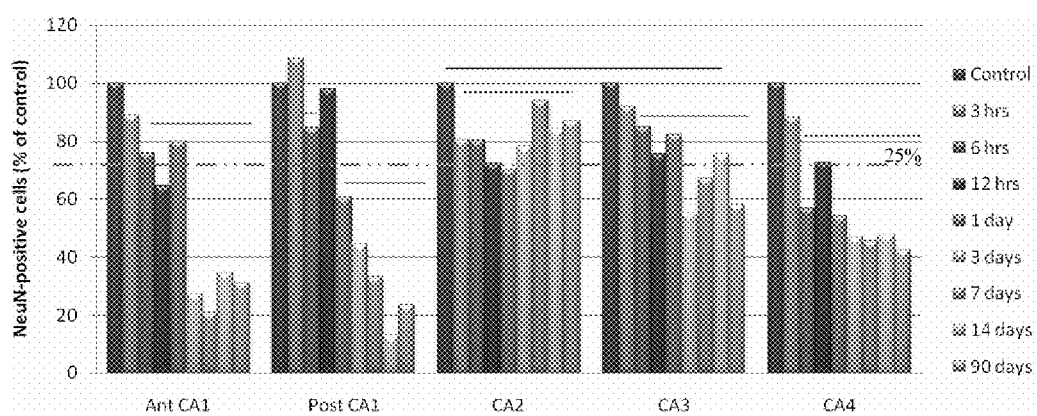
B
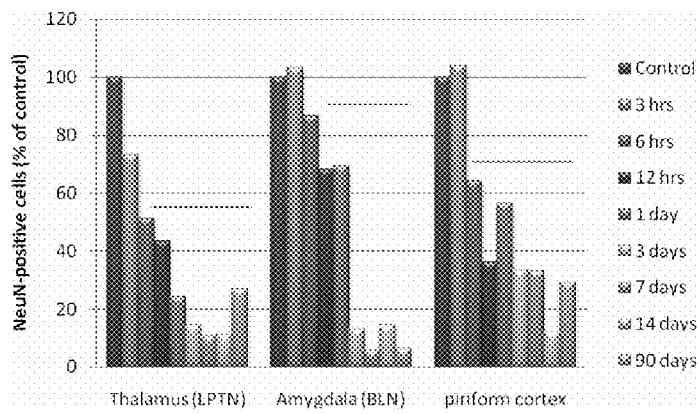

Figure 3

A) Temporal patterning of neurodegeneration following 60 minutes of status epilepticus

Brain Regions
*Subfields of the Hippocampus*

| | Anterior CA1 | Posterior CA1 (D&V) | CA2 | CA3 | CA4 | Amygdala (BLN) | Thalamus (LPTN) | Piriform cortex |
|---|---|---|---|---|---|---|---|---|
| Naïve | 113188±20463 | 88877±14453 | 102286±81017 | 46069±2545 | 46207±6904 | 37905±6980 | 22897±6881 | 34472±8632 |
| 3 hrs | 78815±15948 | 96674±6893 | 79832±62171 | 42371±3086 | 40791±3376 | 39207±7755 | 16790±3796 | 35847±5772 |
| 6 hrs | 86094±7058* | 75234±14932 | 79832±59875* | 39074±9031* | 26267±3597* | 32841±6885* | 11743±5040* | 22181±1129* |
| 12 hrs | 73063±4166* | 87006±2507 | 81094±51144* | 34817±9193* | 33581±9914* | 25896±6345* | 9991±849* | 12498±12432* |
| 24 hrs | 90502±19821* | 53872±8847* | 86071±19946* | 37838±4987* | 25082±7104* | 26186±5456* | 5562±4465* | 19503±11949* |
| 3 days | 30569±17150* | 39527±18036* | 77340±57368* | 23409±10220* | 21621±5614* | 4918±4132* | 3296±2366* | 11339±4511* |
| 7 days | 23540±5959* | 29470±6782* | 94790±58629* | 31040±7951* | 21013±10193* | 2170±3610* | 2472±2874* | 11468±4064* |
| 14 days | 39262±23817* | 11616±3070* | 88567±56133* | 34840±4186* | 22132±14485* | 5497±4394* | 2575±2761* | 4166±3633* |
| 90 days | 42735±34939* | 21018±5448* | 87567±56133* | 26782±8837* | 19674±13152* | 2459±3547* | 8652±7285* | 10026±3127* |

Values are expressed cell density (# cells/mm$^3$) ± standard deviation. Each group had at least 4 animals.
*Different from naïve group (p<0.05).

Tat-NR2B9c is neuroprotective in the anterior CA1 region of the hippocampus

* Different from control animals. # Different from saline and Tat-NR2BAA treated groups. Dots represent individual animals. Dash represents group average.

Animals experienced 60 minutes of Li/pilocarpine-induced SE. Tat-NR2B9C (3 nmol/ g) was administered 10 minutes into SE or 3 hr after the termination of SE. Animals were sacrificed 14 days after the termination of SE. * significantly different from "NO Tat-NR2B9C".

Tat-NR2B9c protects near the subicular border of the CA1 region

** Tat-NR2B9c is different from saline and Tat-NR2B9AA groups (p<0.01)

Tat-NR2B9c is highly neuroprotective in the CA4 region

* Different from control animals. Bar indicates Tat-NR2B9c is different from saline (p<0.05). Dots represent individual animals. Dash represents group average.

Figure 13
Morris water maze
A.
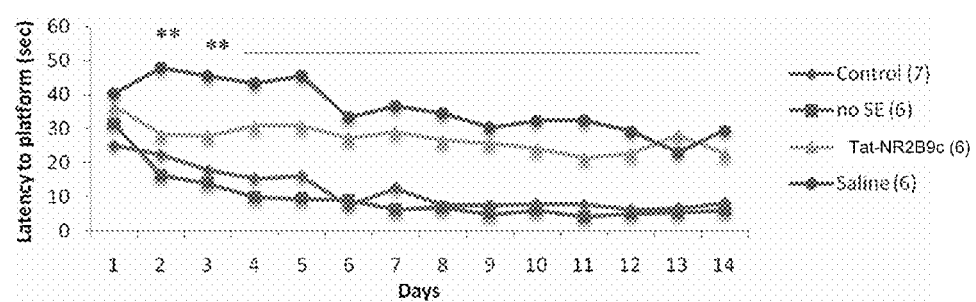
B.
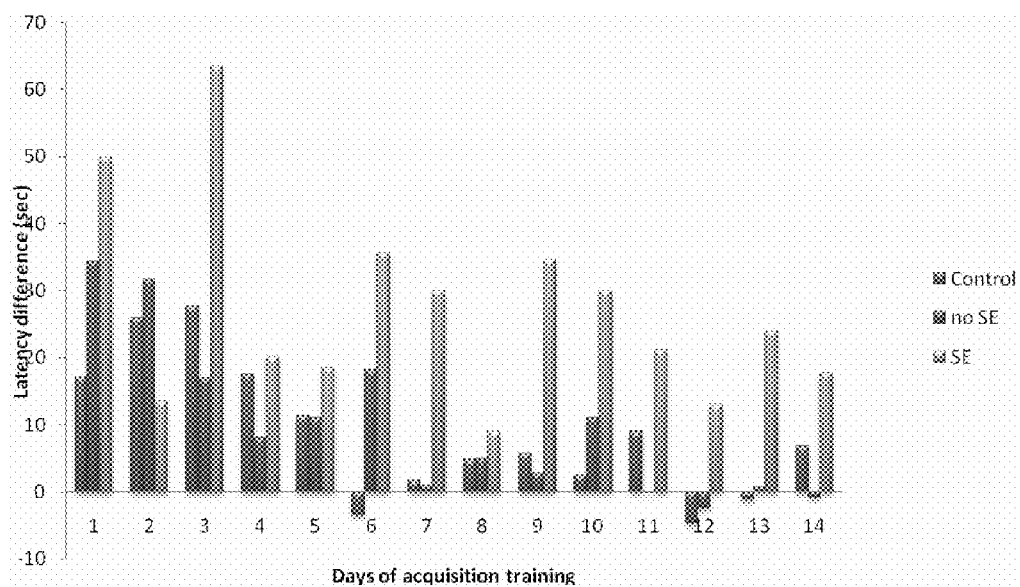

SEQUENCE LISTING

```
<160> NUMBER OF SEQ ID NOS: 102

<210> SEQ ID NO 1
<211> LENGTH: 4
<212> TYPE: PRT
<213> ORGANISM: Artificial Sequence
<220> FEATURE:
<223> OTHER INFORMATION: synthetic C-terminal 4mer active peptide, PDZ-
      binding ligand (PL) motif of N-methyl-D-aspartate (NMDA) receptor
      2A (NMDAR2A), 2B (NMDAR2B) and 3 (NMDAR3)

<400> SEQUENCE: 1

Glu Ser Asp Val
 1

<210> SEQ ID NO 2
<211> LENGTH: 4
<212> TYPE: PRT
<213> ORGANISM: Artificial Sequence
<220> FEATURE:
<223> OTHER INFORMATION: synthetic C-terminal 4mer active peptide, PDZ-
      binding ligand (PL) motif of N-methyl-D-aspartate (NMDA) receptor
      2C (NMDAR2C) or 2D (NMDAR2D)

<400> SEQUENCE: 2

Glu Ser Glu Val
 1

<210> SEQ ID NO 3
<211> LENGTH: 4
<212> TYPE: PRT
<213> ORGANISM: Artificial Sequence
<220> FEATURE:
<223> OTHER INFORMATION: synthetic C-terminal active peptide, PDZ-
      binding ligand (PL) motif

<400> SEQUENCE: 3

Glu Thr Asp Val
 1

<210> SEQ ID NO 4
<211> LENGTH: 4
<212> TYPE: PRT
<213> ORGANISM: Artificial Sequence
<220> FEATURE:
<223> OTHER INFORMATION: synthetic C-terminal active peptide, PDZ-
      binding ligand (PL) motif

<400> SEQUENCE: 4

Glu Thr Glu Val
 1

<210> SEQ ID NO 5
<211> LENGTH: 4
<212> TYPE: PRT
<213> ORGANISM: Artificial Sequence
<220> FEATURE:
<223> OTHER INFORMATION: synthetic C-terminal active peptide, PDZ-
``` binding ligand (PL) motif

<400> SEQUENCE: 5

Asp Thr Asp Val
1

<210> SEQ ID NO 6
<211> LENGTH: 4
<212> TYPE: PRT
<213> ORGANISM: Artificial Sequence
<220> FEATURE:
<223> OTHER INFORMATION: synthetic C-terminal active peptide, PDZ-
      binding ligand (PL) motif

<400> SEQUENCE: 6

Asp Thr Glu Val
1

<210> SEQ ID NO 7
<211> LENGTH: 9
<212> TYPE: PRT
<213> ORGANISM: Artificial Sequence
<220> FEATURE:
<223> OTHER INFORMATION: synthetic active peptide, PDZ-binding ligand
      (PL) motif

<400> SEQUENCE: 7

Lys Leu Ser Ser Ile Glu Thr Asp Val
1               5

<210> SEQ ID NO 8
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to HIV TAT internalization peptide,
      Tat-NR2B9c-(TDV)

<400> SEQUENCE: 8

Tyr Gly Arg Lys Lys Arg Arg Gln Arg Arg Arg Lys Leu Ser Ser Ile
1               5                   10                  15

Glu Thr Asp Val
            20

<210> SEQ ID NO 9
<211> LENGTH: 9
<212> TYPE: PRT
<213> ORGANISM: Artificial Sequence
<220> FEATURE:
<223> OTHER INFORMATION: synthetic active peptide, PDZ-binding ligand
      (PL) motif

<400> SEQUENCE: 9

Lys Leu Ser Ser Ile Glu Ser Asp Val
1               5

<210> SEQ ID NO 10
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to HIV TAT internalization peptide,
      Tat-NR2B9c-(SDV)

<400> SEQUENCE: 10

Tyr Gly Arg Lys Lys Arg Arg Gln Arg Arg Arg Lys Leu Ser Ser Ile
1               5                   10                  15

Glu Ser Asp Val
            20

<210> SEQ ID NO 11
<211> LENGTH: 4
<212> TYPE: PRT
<213> ORGANISM: Artificial Sequence
<220> FEATURE:
<223> OTHER INFORMATION: synthetic post synaptic density protein 95
      (PSD-95), Drosophila disc large (DLG), zonula occludens-1
      (ZO1) (PDZ) domain (DLG homologous region (DHR)) GLGF repeat

<400> SEQUENCE: 11

Gly Leu Gly Phe
1

<210> SEQ ID NO 12
<211> LENGTH: 20
<212> TYPE: PRT
<213> ORGANISM: Artificial Sequence
<220> FEATURE:
<223> OTHER INFORMATION: synthetic N-methyl-D-aspartate (NMDA) receptor
      2B (NMDAR2B) or 3 (NMDAR3) C-terminal 20mer active peptide,
      PDZ-binding ligand (PL) motif

<400> SEQUENCE: 12

Phe Asn Gly Ser Ser Asn Gly His Val Tyr Glu Lys Leu Ser Ser Ile
1               5                   10                  15

Glu Ser Asp Val
            20

<210> SEQ ID NO 13
<211> LENGTH: 20
<212> TYPE: PRT
<213> ORGANISM: Artificial Sequence
<220> FEATURE:
<223> OTHER INFORMATION: synthetic N-methyl-D-aspartate (NMDA) receptor
      1 (NMDAR1), 1-1 (NMDAR1-1), 1-3b (NMDAR1-3b), 1-4 (NMDAR1-4) or
      1-4b (NMDAR1-4b) C-terminal 20mer active peptide, PDZ-binding
      ligand (PL) motif

<400> SEQUENCE: 13

His Pro Thr Asp Ile Thr Gly Pro Leu Asn Leu Ser Asp Pro Ser Val
1               5                   10                  15

Ser Thr Val Val
            20

<210> SEQ ID NO 14
<211> LENGTH: 4
<212> TYPE: PRT
<213> ORGANISM: Artificial Sequence
<220> FEATURE:
<223> OTHER INFORMATION: synthetic N-methyl-D-aspartate (NMDA) receptor
      1 (NMDAR1), 1-1 (NMDAR1-1), 1-3b (NMDAR1-3b), 1-4 (NMDAR1-4) or
      1-4b (NMDAR1-4b) C-terminal 4mer active peptide, PDZ-binding
      ligand (PL) motif

<400> SEQUENCE: 14

Ser Thr Val Val
1

<210> SEQ ID NO 15
<211> LENGTH: 20
<212> TYPE: PRT
<213> ORGANISM: Artificial Sequence

```
<220> FEATURE:
<223> OTHER INFORMATION: synthetic N-methyl-D-aspartate (NMDA) receptor
      1-2 (NMDAR1-2) or 1-3 (NMDAR1-3) C-terminal 20mer active peptide,
      PDZ-binding ligand (PL) motif

<400> SEQUENCE: 15

Arg Arg Ala Ile Glu Arg Glu Glu Gly Gln Leu Gln Leu Cys Ser Arg
1               5                   10                  15

His Arg Glu Ser
            20

<210> SEQ ID NO 16
<211> LENGTH: 4
<212> TYPE: PRT
<213> ORGANISM: Artificial Sequence
<220> FEATURE:
<223> OTHER INFORMATION: synthetic N-methyl-D-aspartate (NMDA) receptor
      1-2 (NMDAR1-2) or 1-3 (NMDAR1-3) C-terminal 4mer active peptide,
      PDZ-binding ligand (PL) motif

<400> SEQUENCE: 16

His Arg Glu Ser
1

<210> SEQ ID NO 17
<211> LENGTH: 20
<212> TYPE: PRT
<213> ORGANISM: Artificial Sequence
<220> FEATURE:
<223> OTHER INFORMATION: synthetic N-methyl-D-aspartate (NMDA) receptor
      2C (NMDAR2C) C-terminal 20mer active peptide, PDZ-binding ligand
      (PL) motif

<400> SEQUENCE: 17

Thr Gln Gly Phe Pro Gly Pro Cys Thr Trp Arg Arg Ile Ser Ser Leu
1               5                   10                  15

Glu Ser Glu Val
            20

<210> SEQ ID NO 18
<211> LENGTH: 20
<212> TYPE: PRT
<213> ORGANISM: Artificial Sequence
<220> FEATURE:
<223> OTHER INFORMATION: synthetic N-methyl-D-aspartate (NMDA) receptor
      3A (NMDAR3A) C-terminal 20mer active peptide, PDZ-binding ligand
      (PL) motif

<400> SEQUENCE: 18

Ala Val Ser Arg Lys Thr Glu Leu Glu Glu Tyr Gln Arg Thr Ser Arg
1               5                   10                  15

Thr Cys Glu Ser
            20

<210> SEQ ID NO 19
<211> LENGTH: 4
<212> TYPE: PRT
<213> ORGANISM: Artificial Sequence
<220> FEATURE:
<223> OTHER INFORMATION: synthetic N-methyl-D-aspartate (NMDA) receptor
      3A (NMDAR3A) C-terminal 4mer active peptide, PDZ-binding ligand
      (PL) motif

<400> SEQUENCE: 19

Thr Cys Glu Ser
1
```

```
<210> SEQ ID NO 20
<211> LENGTH: 20
<212> TYPE: PRT
<213> ORGANISM: Artificial Sequence
<220> FEATURE:
<223> OTHER INFORMATION: synthetic N-methyl-D-aspartate (NMDA) receptor
      2A (NMDAR2A) C-terminal 20mer active peptide, PDZ-binding ligand
      (PL) motif

<400> SEQUENCE: 20

Leu Asn Ser Cys Ser Asn Arg Arg Val Tyr Lys Lys Met Pro Ser Ile
 1               5                  10                  15

Glu Ser Asp Val
            20

<210> SEQ ID NO 21
<211> LENGTH: 20
<212> TYPE: PRT
<213> ORGANISM: Artificial Sequence
<220> FEATURE:
<223> OTHER INFORMATION: synthetic N-methyl-D-aspartate (NMDA) receptor
      2D (NMDAR2D) C-terminal 20mer active peptide, PDZ-binding ligand
      (PL) motif

<400> SEQUENCE: 21

Gly Gly Asp Leu Gly Thr Arg Arg Gly Ser Ala His Phe Ser Ser Leu
 1               5                  10                  15

Glu Ser Glu Val
            20

<210> SEQ ID NO 22
<211> LENGTH: 20
<212> TYPE: PRT
<213> ORGANISM: Artificial Sequence
<220> FEATURE:
<223> OTHER INFORMATION: synthetic glutamate receptor delta 2 C-terminal
      20mer active peptide, PDZ-binding ligand (PL) motif

<400> SEQUENCE: 22

Gln Pro Thr Pro Thr Leu Gly Leu Asn Leu Gly Asn Asp Pro Asp Arg
 1               5                  10                  15

Gly Thr Ser Ile
            20

<210> SEQ ID NO 23
<211> LENGTH: 4
<212> TYPE: PRT
<213> ORGANISM: Artificial Sequence
<220> FEATURE:
<223> OTHER INFORMATION: synthetic glutamate receptor delta 2 C-terminal
      4mer active peptide, PDZ-binding ligand (PL) motif

<400> SEQUENCE: 23

Gly Thr Ser Ile
 1

<210> SEQ ID NO 24
<211> LENGTH: 20
<212> TYPE: PRT
<213> ORGANISM: Artificial Sequence
<220> FEATURE:
<223> OTHER INFORMATION: synthetic glutamate receptor 1 C-terminal 20mer
      active peptide, PDZ-binding ligand (PL) motif

<400> SEQUENCE: 24

Met Gln Ser Ile Pro Cys Met Ser His Ser Ser Gly Met Pro Leu Gly
```

```
                 1               5                  10                  15

Ala Thr Gly Leu
            20

<210> SEQ ID NO 25
<211> LENGTH: 4
<212> TYPE: PRT
<213> ORGANISM: Artificial Sequence
<220> FEATURE:
<223> OTHER INFORMATION: synthetic glutamate receptor 1 C-terminal 4mer
      active peptide, PDZ-binding ligand (PL) motif

<400> SEQUENCE: 25

Ala Thr Gly Leu
 1

<210> SEQ ID NO 26
<211> LENGTH: 20
<212> TYPE: PRT
<213> ORGANISM: Artificial Sequence
<220> FEATURE:
<223> OTHER INFORMATION: synthetic glutamate receptor 2 C-terminal 20mer
      active peptide, PDZ-binding ligand (PL) motif

<400> SEQUENCE: 26

Gln Asn Phe Ala Thr Tyr Lys Glu Gly Tyr Asn Val Tyr Gly Ile Glu
 1               5                  10                  15

Ser Val Lys Ile
            20

<210> SEQ ID NO 27
<211> LENGTH: 4
<212> TYPE: PRT
<213> ORGANISM: Artificial Sequence
<220> FEATURE:
<223> OTHER INFORMATION: synthetic glutamate receptor 2 and 3 C-terminal
      4mer active peptide, PDZ-binding ligand (PL) motif

<400> SEQUENCE: 27

Ser Val Lys Ile
 1

<210> SEQ ID NO 28
<211> LENGTH: 20
<212> TYPE: PRT
<213> ORGANISM: Artificial Sequence
<220> FEATURE:
<223> OTHER INFORMATION: synthetic glutamate receptor 3 C-terminal 20mer
      active peptide, PDZ-binding ligand (PL) motif

<400> SEQUENCE: 28

Gln Asn Tyr Ala Thr Tyr Arg Glu Gly Tyr Asn Val Tyr Gly Thr Glu
 1               5                  10                  15

Ser Val Lys Ile
            20

<210> SEQ ID NO 29
<211> LENGTH: 20
<212> TYPE: PRT
<213> ORGANISM: Artificial Sequence
<220> FEATURE:
<223> OTHER INFORMATION: synthetic glutamate receptor 4 C-terminal 20mer
      active peptide, PDZ-binding ligand (PL) motif

<400> SEQUENCE: 29

His Thr Gly Thr Ala Ile Arg Gln Ser Ser Gly Leu Ala Val Ile Ala
```

```
                 1               5                  10                 15

Ser Asp Leu Pro
            20

<210> SEQ ID NO 30
<211> LENGTH: 4
<212> TYPE: PRT
<213> ORGANISM: Artificial Sequence
<220> FEATURE:
<223> OTHER INFORMATION: synthetic glutamate receptor 4 C-terminal 4mer
      active peptide, PDZ-binding ligand (PL) motif

<400> SEQUENCE: 30

Ser Asp Leu Pro
  1

<210> SEQ ID NO 31
<211> LENGTH: 20
<212> TYPE: PRT
<213> ORGANISM: Artificial Sequence
<220> FEATURE:
<223> OTHER INFORMATION: synthetic glutamate receptor 5 C-terminal 20mer
      active peptide, PDZ-binding ligand (PL) motif

<400> SEQUENCE: 31

Ser Phe Thr Ser Ile Leu Thr Cys His Gln Arg Arg Thr Gln Arg Lys
  1               5                  10                 15

Glu Thr Val Ala
            20

<210> SEQ ID NO 32
<211> LENGTH: 4
<212> TYPE: PRT
<213> ORGANISM: Artificial Sequence
<220> FEATURE:
<223> OTHER INFORMATION: synthetic glutamate receptor 5 C-terminal 4mer
      active peptide, PDZ-binding ligand (PL) motif

<400> SEQUENCE: 32

Glu Thr Val Ala
  1

<210> SEQ ID NO 33
<211> LENGTH: 20
<212> TYPE: PRT
<213> ORGANISM: Artificial Sequence
<220> FEATURE:
<223> OTHER INFORMATION: synthetic glutamate receptor 6 C-terminal 20mer
      active peptide, PDZ-binding ligand (PL) motif

<400> SEQUENCE: 33

Glu Val Ile Asn Met His Thr Phe Asn Asp Arg Arg Leu Pro Gly Lys
  1               5                  10                 15

Glu Thr Met Ala
            20

<210> SEQ ID NO 34
<211> LENGTH: 4
<212> TYPE: PRT
<213> ORGANISM: Artificial Sequence
<220> FEATURE:
<223> OTHER INFORMATION: synthetic glutamate receptor 6 C-terminal 4mer
      active peptide, PDZ-binding ligand (PL) motif

<400> SEQUENCE: 34

Glu Thr Met Ala
```

```
<210> SEQ ID NO 35
<211> LENGTH: 20
<212> TYPE: PRT
<213> ORGANISM: Artificial Sequence
<220> FEATURE:
<223> OTHER INFORMATION: synthetic glutamate receptor 7 C-terminal 20mer
      active peptide, PDZ-binding ligand (PL) motif

<400> SEQUENCE: 35

Arg Arg Leu Pro Gly Lys Asp Ser Met Ala Cys Ser Thr Ser Leu Ala
 1               5                  10                  15

Pro Val Phe Pro
            20

<210> SEQ ID NO 36
<211> LENGTH: 4
<212> TYPE: PRT
<213> ORGANISM: Artificial Sequence
<220> FEATURE:
<223> OTHER INFORMATION: synthetic glutamate receptor 7 C-terminal 4mer
      active peptide, PDZ-binding ligand (PL) motif

<400> SEQUENCE: 36

Pro Val Phe Pro
 1

<210> SEQ ID NO 37
<211> LENGTH: 4
<212> TYPE: PRT
<213> ORGANISM: Artificial Sequence
<220> FEATURE:
<223> OTHER INFORMATION: synthetic C-terminal active peptide, PDZ-
      binding ligand (PL) motif

<400> SEQUENCE: 37

Glu Ser Thr Val
 1

<210> SEQ ID NO 38
<211> LENGTH: 11
<212> TYPE: PRT
<213> ORGANISM: Artificial Sequence
<220> FEATURE:
<223> OTHER INFORMATION: synthetic HIV TAT internalization peptide

<400> SEQUENCE: 38

Tyr Gly Arg Lys Lys Arg Arg Gln Arg Arg
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: synthetic variant peptide of HIV TAT
      internalization peptide with reduced N-type calcium channel
      binding
<221> NAME/KEY: MOD_RES
<222> LOCATION: (1)...(1)
<223> OTHER INFORMATION: Xaa = any amino acid other than Tyr

<400> SEQUENCE: 39

Xaa Gly Arg Lys Lys Arg Arg Gln Arg Arg
 1               5                  10
```

```
<210> SEQ ID NO 40
<211> LENGTH: 11
<212> TYPE: PRT
<213> ORGANISM: Artificial Sequence
<220> FEATURE:
<223> OTHER INFORMATION: synthetic preferred variant peptide where N-
      terminal Tyr residue substituted with Phe of HIV TAT
      internalization peptide with reduced N-type calcium channel
      binding

<400> SEQUENCE: 40

Phe Gly Arg Lys Lys Arg Arg Gln Arg Arg Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: synthetic preferred variant peptide of HIV TAT
      internalization peptide with reduced N-type calcium channel
      binding

<400> SEQUENCE: 41

Gly Arg Lys Lys Arg Arg Gln Arg Arg Arg
1               5                   10

<210> SEQ ID NO 42
<211> LENGTH: 5
<212> TYPE: PRT
<213> ORGANISM: Artificial Sequence
<220> FEATURE:
<223> OTHER INFORMATION: synthetic spacer or linker amino acids to join
      peptide domains

<400> SEQUENCE: 42

Gly Ser Ser Ser Ser
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic spacer or linker amino acids to join
      peptide domains

<400> SEQUENCE: 43

Thr Gly Glu Lys Pro
1               5

<210> SEQ ID NO 44
<211> LENGTH: 8
<212> TYPE: PRT
<213> ORGANISM: Artificial Sequence
<220> FEATURE:
<223> OTHER INFORMATION: synthetic spacer or linker amino acids to join
      peptide domains

<400> SEQUENCE: 44

Gly Gly Arg Arg Gly Gly Gly Ser
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic spacer or linker amino acids to join
```

-continued peptide domains

<400> SEQUENCE: 45

Leu Arg Gln Arg Asp Gly Glu Arg Pro
1               5

<210> SEQ ID NO 46
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide, F-TatNR2B9c-(SDV)
<221> NAME/KEY: MOD_RES
<222> LOCATION: (1)...(1)
<223> OTHER INFORMATION: Phe may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 46

Phe Gly Arg Lys Lys Arg Arg Gln Arg Arg Arg Lys Leu Ser Ser Ile
1               5                   10                  15

Glu Ser Asp Val
            20

<210> SEQ ID NO 47
<211> LENGTH: 21
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide, F-TatNR2B9c-(SDV)
<221> NAME/KEY: MOD_RES
<222> LOCATION: (1)...(1)
<223> OTHER INFORMATION: Xaa = pyroglutamate

<400> SEQUENCE: 47

Xaa Phe Gly Arg Lys Lys Arg Arg Gln Arg Arg Arg Lys Leu Ser Ser
1               5                   10                  15

Ile Glu Ser Asp Val
            20

<210> SEQ ID NO 48
<211> LENGTH: 21
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide, F-TatNR2B9c-(SDV)
<221> NAME/KEY: MOD_RES
<222> LOCATION: (1)...(1)
<223> OTHER INFORMATION: Xaa = any amino acid other than Tyr

<400> SEQUENCE: 48

Xaa Phe Gly Arg Lys Lys Arg Arg Gln Arg Arg Arg Lys Leu Ser Ser
1               5                   10                  15

Ile Glu Ser Asp Val
            20

<210> SEQ ID NO 49
<211> LENGTH: 19
<212> TYPE: PRT
<213> ORGANISM: Artificial Sequence
<220> FEATURE:

```
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Gly may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 49

Gly Lys Lys Lys Lys Lys Gln Lys Lys Lys Lys Leu Ser Ser Ile Glu
1               5                   10                  15

Ser Asp Val

<210> SEQ ID NO 50
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 50

Xaa Gly Lys Lys Lys Lys Lys Gln Lys Lys Lys Lys Leu Ser Ser Ile
1               5                   10                  15

Glu Ser Asp Val
            20

<210> SEQ ID NO 51
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 51

Xaa Gly Lys Lys Lys Lys Lys Gln Lys Lys Lys Lys Leu Ser Ser Ile
1               5                   10                  15

Glu Ser Asp Val
            20

<210> SEQ ID NO 52
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 52

Arg Lys Lys Arg Arg Gln Arg Arg Arg Lys Leu Ser Ser Ile Glu Ser
1               5                   10                  15
```

-continued

Asp Val

<210> SEQ ID NO 53
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 53

Xaa Arg Lys Lys Arg Arg Gln Arg Arg Arg Lys Leu Ser Ser Ile Glu
 1               5                   10                  15

Ser Asp Val

<210> SEQ ID NO 54
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 54

Xaa Arg Lys Lys Arg Arg Gln Arg Arg Arg Lys Leu Ser Ser Ile Glu
 1               5                   10                  15

Ser Asp Val

<210> SEQ ID NO 55
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Gly may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 55

Gly Ala Lys Lys Arg Arg Gln Arg Arg Arg Lys Leu Ser Ser Ile Glu
 1               5                   10                  15

Ser Asp Val

<210> SEQ ID NO 56
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

```
<400> SEQUENCE: 56

Xaa Gly Ala Lys Lys Arg Arg Gln Arg Arg Arg Lys Leu Ser Ser Ile
 1               5                  10                  15

Glu Ser Asp Val
            20

<210> SEQ ID NO 57
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 57

Xaa Gly Ala Lys Lys Arg Arg Gln Arg Arg Arg Lys Leu Ser Ser Ile
 1               5                  10                  15

Glu Ser Asp Val
            20

<210> SEQ ID NO 58
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Ala may be modified by biotin, a capping moiety
      including acetyl, benzoyl, aliphatic alkyl or alkyl with
      cycloalkyl, biotin with alkyl spacer or 5,6-carboxyfluorescein
      (5,6-FAM)

<400> SEQUENCE: 58

Ala Lys Lys Arg Arg Gln Arg Arg Arg Lys Leu Ser Ser Ile Glu Ser
 1               5                  10                  15

Asp Val

<210> SEQ ID NO 59
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 59

Xaa Ala Lys Lys Arg Arg Gln Arg Arg Arg Lys Leu Ser Ser Ile Glu
 1               5                  10                  15

Ser Asp Val

<210> SEQ ID NO 60
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
```

```
            motif active peptide linked to variant peptide of HIV TAT
            internalization peptide
<221> NAME/KEY: MOD_RES
<222> LOCATION: (1)...(1)
<223> OTHER INFORMATION: Xaa = any amino acid other than Tyr

<400> SEQUENCE: 60

Xaa Ala Lys Lys Arg Arg Gln Arg Arg Arg Lys Leu Ser Ser Ile Glu
 1               5                  10                  15

Ser Asp Val

<210> SEQ ID NO 61
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Gly may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 61

Gly Arg Lys Ala Arg Arg Gln Arg Arg Arg Lys Leu Ser Ser Ile Glu
 1               5                  10                  15

Ser Asp Val

<210> SEQ ID NO 62
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 62

Xaa Gly Arg Lys Ala Arg Arg Gln Arg Arg Arg Lys Leu Ser Ser Ile
 1               5                  10                  15

Glu Ser Asp Val
            20

<210> SEQ ID NO 63
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 63

Xaa Gly Arg Lys Ala Arg Arg Gln Arg Arg Arg Lys Leu Ser Ser Ile
 1               5                  10                  15

Glu Ser Asp Val
            20
```

```
<210> SEQ ID NO 64
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 64

Arg Lys Ala Arg Arg Gln Arg Arg Arg Lys Leu Ser Ser Ile Glu Ser
 1               5                   10                  15

Asp Val

<210> SEQ ID NO 65
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 65

Xaa Arg Lys Ala Arg Arg Gln Arg Arg Arg Lys Leu Ser Ser Ile Glu
 1               5                   10                  15

Ser Asp Val

<210> SEQ ID NO 66
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 66

Xaa Arg Lys Ala Arg Arg Gln Arg Arg Arg Lys Leu Ser Ser Ile Glu
 1               5                   10                  15

Ser Asp Val

<210> SEQ ID NO 67
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Gly may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 67
```

Gly Arg Lys Lys Ala Arg Gln Arg Arg Arg Lys Leu Ser Ser Ile Glu
1               5                   10                  15

Ser Asp Val

<210> SEQ ID NO 68
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 68

Xaa Gly Arg Lys Lys Ala Arg Gln Arg Arg Arg Lys Leu Ser Ser Ile
1               5                   10                  15

Glu Ser Asp Val
            20

<210> SEQ ID NO 69
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 69

Xaa Gly Arg Lys Lys Ala Arg Gln Arg Arg Arg Lys Leu Ser Ser Ile
1               5                   10                  15

Glu Ser Asp Val
            20

<210> SEQ ID NO 70
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping
      moiety including acetyl, benzoyl, aliphatic alkyl or alkyl with
      cycloalkyl, biotin with alkyl spacer or 5,6-carboxyfluorescein
      (5,6-FAM)

<400> SEQUENCE: 70

Arg Lys Lys Ala Arg Gln Arg Arg Arg Lys Leu Ser Ser Ile Glu Ser
1               5                   10                  15

Asp Val

<210> SEQ ID NO 71
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT

```
          internalization peptide
<221> NAME/KEY: MOD_RES
<222> LOCATION: (1)...(1)
<223> OTHER INFORMATION: Xaa = pyroglutamate

<400> SEQUENCE: 71

Xaa Arg Lys Lys Ala Arg Gln Arg Arg Arg Lys Leu Ser Ser Ile Glu
 1               5                  10                  15

Ser Asp Val

<210> SEQ ID NO 72
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 72

Xaa Arg Lys Lys Ala Arg Gln Arg Arg Arg Lys Leu Ser Ser Ile Glu
 1               5                  10                  15

Ser Asp Val

<210> SEQ ID NO 73
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Gly may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 73

Gly Arg Lys Lys Arg Arg Gln Ala Arg Arg Lys Leu Ser Ser Ile Glu
 1               5                  10                  15

Ser Asp Val

<210> SEQ ID NO 74
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 74

Xaa Gly Arg Lys Lys Arg Arg Gln Ala Arg Arg Lys Leu Ser Ser Ile
 1               5                  10                  15

Glu Ser Asp Val
            20

<210> SEQ ID NO 75
<211> LENGTH: 20
```

```
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 75

Xaa Gly Arg Lys Lys Arg Arg Gln Ala Arg Arg Lys Leu Ser Ser Ile
1               5                   10                  15

Glu Ser Asp Val
            20

<210> SEQ ID NO 76
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 76

Arg Lys Lys Arg Arg Gln Ala Arg Arg Lys Leu Ser Ser Ile Glu Ser
1               5                   10                  15

Asp Val

<210> SEQ ID NO 77
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 77

Xaa Arg Lys Lys Arg Arg Gln Ala Arg Arg Lys Leu Ser Ser Ile Glu
1               5                   10                  15

Ser Asp Val

<210> SEQ ID NO 78
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 78

Xaa Arg Lys Lys Arg Arg Gln Ala Arg Arg Lys Leu Ser Ser Ile Glu
1               5                   10                  15
```

Ser Asp Val

<210> SEQ ID NO 79
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Gly may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 79

Gly Arg Lys Lys Arg Arg Gln Arg Ala Arg Lys Leu Ser Ser Ile Glu
1               5                   10                  15

Ser Asp Val

<210> SEQ ID NO 80
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 80

Xaa Gly Arg Lys Lys Arg Arg Gln Arg Ala Arg Lys Leu Ser Ser Ile
1               5                   10                  15

Glu Ser Asp Val
            20

<210> SEQ ID NO 81
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 81

Xaa Gly Arg Lys Lys Arg Arg Gln Arg Ala Arg Lys Leu Ser Ser Ile
1               5                   10                  15

Glu Ser Asp Val
            20

<210> SEQ ID NO 82
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety including acetyl, benzoyl, aliphatic alkyl or
alkyl with cycloalkyl, biotin with alkyl spacer or
5,6-carboxyfluorescein (5,6-FAM)

<400> SEQUENCE: 82

Arg Lys Lys Arg Arg Gln Arg Ala Arg Lys Leu Ser Ser Ile Glu Ser
1               5                   10                  15

Asp Val

<210> SEQ ID NO 83
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 83

Xaa Arg Lys Lys Arg Arg Gln Arg Ala Arg Lys Leu Ser Ser Ile Glu
1               5                   10                  15

Ser Asp Val

<210> SEQ ID NO 84
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 84

Xaa Arg Lys Lys Arg Arg Gln Arg Ala Arg Lys Leu Ser Ser Ile Glu
1               5                   10                  15

Ser Asp Val

<210> SEQ ID NO 85
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 85

Arg Arg Pro Arg Arg Pro Arg Arg Pro Arg Arg Lys Leu Ser Ser Ile
1               5                   10                  15

Glu Ser Asp Val
            20

<210> SEQ ID NO 86
<211> LENGTH: 21
<212> TYPE: PRT

```
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 86

Xaa Arg Arg Pro Arg Arg Pro Arg Arg Pro Arg Lys Leu Ser Ser
1               5                   10                  15

Ile Glu Ser Asp Val
            20

<210> SEQ ID NO 87
<211> LENGTH: 21
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 87

Xaa Arg Arg Pro Arg Arg Pro Arg Arg Pro Arg Lys Leu Ser Ser
1               5                   10                  15

Ile Glu Ser Asp Val
            20

<210> SEQ ID NO 88
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 88

Arg Arg Ala Arg Arg Ala Arg Arg Ala Arg Arg Lys Leu Ser Ser Ile
1               5                   10                  15

Glu Ser Asp Val
            20

<210> SEQ ID NO 89
<211> LENGTH: 21
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 89

Xaa Arg Arg Ala Arg Arg Ala Arg Arg Ala Arg Arg Lys Leu Ser Ser
1               5                   10                  15
```

Ile Glu Ser Asp Val
            20

<210> SEQ ID NO 90
<211> LENGTH: 21
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 90

Xaa Arg Arg Ala Arg Arg Ala Arg Arg Ala Arg Arg Lys Leu Ser Ser
 1               5                  10                  15

Ile Glu Ser Asp Val
            20

<210> SEQ ID NO 91
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 91

Arg Arg Arg Ala Arg Arg Arg Ala Arg Arg Lys Leu Ser Ser Ile Glu
 1               5                  10                  15

Ser Asp Val

<210> SEQ ID NO 92
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 92

Xaa Arg Arg Arg Ala Arg Arg Arg Ala Arg Arg Lys Leu Ser Ser Ile
 1               5                  10                  15

Glu Ser Asp Val
            20

<210> SEQ ID NO 93
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES

```
<222> LOCATION: (1)...(1)
<223> OTHER INFORMATION: Xaa = any amino acid other than Tyr

<400> SEQUENCE: 93

Xaa Arg Arg Arg Ala Arg Arg Ala Arg Arg Lys Leu Ser Ser Ile
1               5                   10                  15

Glu Ser Asp Val
            20

<210> SEQ ID NO 94
<211> LENGTH: 19
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 94

Arg Arg Arg Pro Arg Arg Arg Pro Arg Arg Lys Leu Ser Ser Ile Glu
1               5                   10                  15

Ser Asp Val

<210> SEQ ID NO 95
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 95

Xaa Arg Arg Arg Pro Arg Arg Arg Pro Arg Arg Lys Leu Ser Ser Ile
1               5                   10                  15

Glu Ser Asp Val
            20

<210> SEQ ID NO 96
<211> LENGTH: 20
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 96

Xaa Arg Arg Arg Pro Arg Arg Arg Pro Arg Arg Lys Leu Ser Ser Ile
1               5                   10                  15

Glu Ser Asp Val
            20

<210> SEQ ID NO 97
<211> LENGTH: 17
```

```
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 97

Arg Arg Pro Arg Arg Pro Arg Arg Lys Leu Ser Ser Ile Glu Ser Asp
 1               5                  10                 15

Val

<210> SEQ ID NO 98
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 98

Xaa Arg Arg Pro Arg Arg Pro Arg Arg Lys Leu Ser Ser Ile Glu Ser
 1               5                  10                 15

Asp Val

<210> SEQ ID NO 99
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 99

Xaa Arg Arg Pro Arg Arg Pro Arg Arg Lys Leu Ser Ser Ile Glu Ser
 1               5                  10                 15

Asp Val

<210> SEQ ID NO 100
<211> LENGTH: 17
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Arg may be modified by biotin, a capping moiety
      including acetyl, benzoyl, aliphatic alkyl or
      alkyl with cycloalkyl, biotin with alkyl spacer or
      5,6-carboxyfluorescein (5,6-FAM)

<400> SEQUENCE: 100

Arg Arg Ala Arg Arg Ala Arg Arg Lys Leu Ser Ser Ile Glu Ser Asp
```

```
                    1               5              10              15
Val

<210> SEQ ID NO 101
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = pyroglutamate

<400> SEQUENCE: 101

Xaa Arg Arg Ala Arg Arg Ala Arg Arg Lys Leu Ser Ser Ile Glu Ser
 1               5                  10                  15

Asp Val

<210> SEQ ID NO 102
<211> LENGTH: 18
<212> TYPE: PRT
<213> ORGANISM: Artificial Sequence
<220> FEATURE:
<223> OTHER INFORMATION: synthetic chimeric PDZ-binding ligand (PL)
      motif active peptide linked to variant peptide of HIV TAT
      internalization peptide
<221> NAME/KEY: MOD_RES
<222> LOCATION: (1)...(1)
<223> OTHER INFORMATION: Xaa = any amino acid other than Tyr

<400> SEQUENCE: 102

Xaa Arg Arg Ala Arg Arg Ala Arg Arg Lys Leu Ser Ser Ile Glu Ser
 1               5                  10                  15

Asp Val
```

TREATMENT FOR EPILEPSY

This application claims the benefit of U.S. Provisional App. No. 61/054,109, filed May 16, 2008, which is hereby incorporated by reference in its entirety for all purposes.

REFERENCE TO A SEQUENCE LISTING

This application includes an electronic sequence listing, provided as an ASCII text file named 110USSEQLISTAS-FILED.txt, of size 43,667 bytes and created on May 12, 2009, which is hereby incorporated by reference in its entirety for all purposes.

BACKGROUND OF THE INVENTION

Epilepsy is a neurological condition characterized by recurrent, unprovoked seizures (Blume et al., Epilepsia. 2001; 42:1212-1218). These seizures are transient signs and/or symptoms due to abnormal, excessive or synchronous neuronal activity in the brain (Fisher et al., Epilepsia 46 (4): 470-2). Epilepsy should not be understood as a single disorder, but rather as a group of syndromes with vastly divergent symptoms but all involving episodic abnormal electrical activity in the brain. It is one of the most common serious neurological disorders in the United States and often requires long-term management. Each year 150000 people in the United States are newly diagnosed as having epilepsy, with the cumulative lifetime incidence approaching 3% (Hauser et al., Epilepsia. 1991; 32:429-445; Begley et al., Epilepsia. 1994; 35:1230-1243). The incidence is highest during the first year of life and in elderly persons. Id. 30% to 40% of patients continue to have seizures despite the use of existing antiepileptic drugs either alone or in combination (Kwan et al., N Engl J. Med. 2000; 342:314-319). Patients with uncontrolled seizures experience significant morbidity and mortality and face social stigma and discrimination as well.

Known anti-epileptic drugs include "traditional" medications such as phenobarbital, primidone, phenyloin, carbamazepine, and valproate; as well as newer antiepileptic drugs that induce voltage-dependent ion channel blockade, enhancement of inhibitory neurotransmission, and/or reduction of excitatory neurotransmission. Examples include glutamate antagonism at N-methyl-D-aspartate (NMDA) receptors (e.g., felbamate) and α-amino-3-hydroxy-5-methyl-4-isoxazole propionic acid (AMPA) receptors (e.g., felbamate, topiramate) and inhibition of γ-aminobutyric acid (GABA) reuptake in neurons and astrocytes (e.g., tiagabine).

Post synaptic density protein 95 (PSD-95) couples NMDARs to pathways mediating excitotoxicity and ischemic brain damage (Aarts et al., Science 298, 846-850 (2002)). This coupling was disrupted by transducing neurons with peptides that bind to modular domains on either side of the PSD-95/NMDAR interaction complex. This treatment attenuated downstream NMDAR signaling without blocking NMDAR activity, protected cultured cortical neurons from excitotoxic insults and reduced cerebral infarction volume in rats subjected to transient focal cerebral ischemia. This result has led to the proposal to use peptide antagonists of PSD-95/NMDAR for treating stroke and other diseases mediated by excitotoxicity. No significant side effects have been observed in phase I trials of one such antagonist.

BRIEF SUMMARY OF THE INVENTION

The invention provides methods of treating or effecting prophylaxis of a patient having or at risk of developing symptoms of epilepsy, comprising administering to the patient an effective regime of an agent that inhibits specific binding of PSD-95 PDZ domains to a PDZ-binding ligand (also called "PL"), e.g., an NMDA receptor. Optionally, the agent is a chimeric peptide comprising an active peptide having an amino acid sequence consisting of 3-25 amino acids from the C-terminus of an NMDA receptor or a PDZ domain 1 and/or 2 from a PSD-95 receptor linked to an internalization peptide. Optionally, the active peptide has an amino acid sequence comprising [E/D/N/Q]-[S/T]-[D/E/Q/N]-[V/L]. Optionally, the active peptide comprises a carboxyl terminal amino acid sequence selected from the group consisting of ESDV (SEQ ID NO:1), ESEV (SEQ ID NO:2), ETDV (SEQ ID NO:3), ETEV (SEQ ID NO:4), DTDV (SEQ ID NO:5), DTEV (SEQ ID NO:6). Optionally, the active peptide has an amino acid sequence comprising KLSSIETDV (SEQ ID NO:7). Optionally, the chimeric peptide has an amino acid comprising YGRKKRRQRRRKLSSIETDV (SEQ ID NO: 8). Optionally, the chimeric peptide has an amino acid sequence consisting of YGRKKRRQRRRKLSSIETDV (SEQ ID NO:8). Optionally, the active peptide has an amino acid sequence comprising KLSSIESDV (SEQ ID NO:9). Optionally, the chimeric peptide has an amino acid sequence comprising YGRKKRRQRRRKLSSIESDV (SEQ ID NO:10). Optionally, the amino acid sequence consists of YGRKKRRQRRRKLSSIESDV (SEQ ID NO:10).

The invention also provides a method of treating epilepsy comprising administering an effective regime of an inhibitor of PSD-95 which blocks binding of a PDZ-binding ligand to a PDZ domain of PSD-95. Optionally, the PDZ domain of PSD-95 is PSD-95 PDZ domain 2. Optionally, the inhibitor is administered at least about one hour after initiation of an episode of epilepsy, for example at least about three hours after initiation of an episode of epilepsy. This can be especially suitable when the episode has a duration of less than about 10 minutes. Optionally, the inhibitor is administered at least about one hour after termination of an episode of epilepsy. For example, the inhibitor is administered at least about three hours after termination of an episode of epilepsy. If desired, the inhibitor is administered not later than about 1 week, e.g., not later than 1 day, after termination of an episode of epilepsy. Optionally, the inhibitor is Tat-NR2B9c. Optionally, the inhibitor is F-Tat-NR2B9c. Optionally, the inhibitor has the structure:

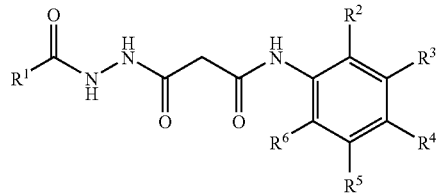

For example, the inhibitor is 0625-0057. The initiation, termination and/or duration of the episode of epilepsy can determined using electroencephalography, e.g., by video electroencephalographic (V-EEG) monitoring.

In a preferred method, the agent can be administered at least one hour after an episode of epilepsy (e.g., a seizure). The agent can be administered for example at least about three, four five, six, eight, ten, twelve, sixteen or twenty four hours after an episode of epilepsy. The agent can also be administered days after the epilepsy episode, e.g., at least about 1, 2, 3, 4, 5, 7, 8, 9, 10 or 12 days after initiation. The agent can also be administered at least a week after the epilepsy episode, e.g., at least about 1, 2 or 3 weeks after the episode. Optionally, the inhibitor is administered after the epilepsy episode but not later than one or more hours, e.g., not later than about 1, 2, 3, 4, 5, 6, 7, 8, 10, 12, 18 or 24 hours after the episode. Optionally, the inhibitor is administered after the epilepsy episode but not later than one or more days, e.g., not later than about 1, 2, 3, 4, 5, 6, 7, 8, 9, 10, 11, 12, or 14 days after the episode. Optionally, the inhibitor is administered after the epilepsy episode but not later than one or more weeks, e.g., not later than about 1, 1.5, 2, 2.5 or 3 weeks after the episode.

Optionally, the timing of administration after an episode of epilepsy can be measured from the time of initiation of the episode (e.g., when the episode is short), or from the time of conclusion of an episode (e.g., when an epileptic seizure is of longer duration), or from any timepoint in where signs of epileptic activity in the brain are observed.

Optionally, the agent is not administered before or during an episode of epilepsy. In other instances, the agent can also be administered during an epileptic episode, e.g., a seizure.

Optionally, the patient is free of diseases other than epilepsy requiring treating with the antagonist. Optionally, the patient is free of diseases other than epilepsy mediated by excitotoxicity. Optionally, the patient is free of stroke. Optionally, the patient is free of diseases mediated by excitotoxicity. Optionally, the agent is administered responsive to the patient having experienced an event promoting epilepsy. Optionally, the patient has an episode of acute epilepsy.

Optionally, the effective regime is administered responsive to diagnosis of epilepsy in the patient. Optionally, the method further comprises administering a second regime effective for treatment or effecting prophylaxis of epilepsy. Optionally, the second regime comprises administering a second agent. Optionally, the second regime comprises an antiepileptic agent or combination of antiepileptic agents.

In some methods, the patient is human. Optionally, the agent is administered by intravenous infusion or subcutaneously. Optionally, the agent is administered together with a pharmaceutically acceptable carrier as a pharmaceutical composition.

Some methods further comprise monitoring the patient to assess the effects of treatment on a symptom and/or sign of epilepsy. Optionally, the chimeric peptide is administered at a dose of from 0.05 to 500 mg, optionally 0.1 to 100 mg, 0.5 to 50 mg, or 1-20 mg.

The invention further provides a pharmaceutical composition for prophylaxis or treatment of symptoms of epilepsy in a patient comprising a pharmaceutically acceptable carrier and an agent as defined above. Optionally, the pharmaceutical composition bears a label indicating suitability for treating or effecting prophylaxis of symptoms of epilepsy.

The invention further provides the use of an agent as defined above in the manufacture of a medicament for treatment or effecting prophylaxis of epilepsy.

The invention further provides methods of treating or effecting prophylaxis of symptoms of epilepsy a patient suffering from or at risk of epilepsy comprising administering to the patient an effective regime of a tSXV peptide linked to an internalization peptide.

Optionally, the effective regime is administered after diagnosis of a symptom of epilepsy in the patient to relieve the symptom, or arrest or inhibit further development of the symptom.

BRIEF DESCRIPTION OF THE DRAWINGS

FIG. 1. Decrease in neuronal cells over time after epileptic seizure. (A) View of brain sections showing number of cells stained using NeuN (a neuron-specific) antibody in naïve rats and rats at 3, 24 and 3 days after induction of epileptic seizures. (B) Quantitative time course of NeuN-positive cell density after termination of epileptic seizures (status epilepticus).

FIG. 2. (A) Neuronal cell decrease in various portions of the hippocampus at various timepoints after epileptic seizure. For each region, columns from left to right indicate percent NeuN-positive cells (compared to control) in the control, at 3 hours, at 6 hours, at 12 hours, at 1 day, at 3 days, at 7 days, at 14 days and at 90 days after epileptic seizure. (B) Rapid and severe cell loss occurs in other brain regions. A total of 4-8 animals were in each group.

FIG. 3. Temporal patterning of neurodegeneration following 60 minutes of status epilepticus. Values are expressed cell density (# cells/mm$^3$)±standard deviation. Each group had at least 4 animals.

FIG. 13. Visual-spatial memory as tested by the Morris water maze at 8 weeks post-SE to detect chronic cognitive impairment. Tat-NR2B9c treatment improves escape latency performance, especially during the initial 5 days of acquisition learning.

DEFINITIONS

Figure 4A:
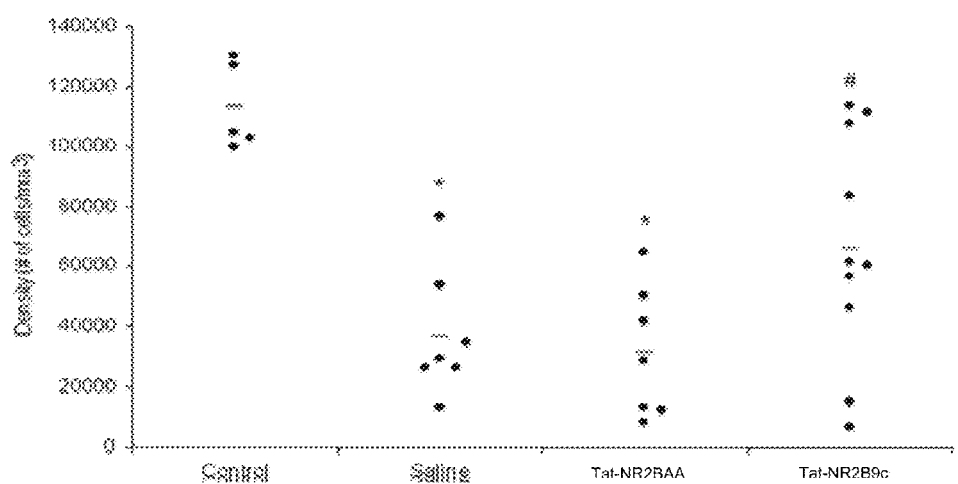
FIG. 4. (A) Tat-NR2B9c but not Tat-NR2BAA is neuroprotective in the anterior CA1 region of the hippocampus. Each dot represents an individual animal. A dash represents a group average. (B) Tat-NR2B9c was neuroprotective when administered after, but not during, epileptic seizure.

A "chimeric polypeptide" refers to a composite polypeptide, i.e., a single contiguous amino acid sequence, made up of two (or more) distinct, heterologous polypeptides which are not normally fused together in a single amino acid sequence.

The term "PDZ domain" refers to a modular protein domain of about 90 amino acids, characterized by significant sequence identity (e.g., at least 60%) to the brain synaptic protein PSD-95, the septate junction protein Drosophila discs large (DLG), and the epithelial tight junction protein zonula occludens-1 protein (ZO1). PDZ domains are also known as DLG homologous regions ("DHRs") and GLGF (SEQ ID NO:11) repeats. PDZ domains generally appear to maintain a core consensus sequence (Doyle, D. A., 1996, Cell 85: 1067-76). Exemplary PDZ domain-containing proteins and PDZ domain sequences disclosed in US 2006-0148711 A1, which is herein incorporated by reference in its entirety.

The term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 3-25 residues, e.g. 3, 4, 5, 8, 10, 12, 14 or 16 residues), forms such a molecular complex. The molecular complex can be observed in vitro using the "A assay" or "G assay" described, e.g., in US 2006-0148711 A1 or in vivo.

A "PL motif" refers to the amino acid sequence of the C-terminus of a PL protein (e.g., the C-terminal 3, 4, 5, 6, 7, 8, 9, 10, 12, 14, 16, 20 or 25 contiguous residues) ("C-terminal PL sequence") or to an internal sequence known to bind a PDZ domain ("internal PL sequence").

A "PL peptide" is a peptide of comprising or consisting of, or otherwise based on, a PL motif that specifically binds to a PDZ domain.

The terms "isolated" or "purified" means that the object species (e.g., a peptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species.

A "peptidomimetic" and refers to a synthetic chemical compound which has substantially the same structural and/or functional characteristics of a peptide of the invention. The peptidomimetic can contain entirely synthetic, non-natural analogues of amino acids, or, is a chimeric molecule of partly natural peptide amino acids and partly non-natural analogs of amino acids. The peptidomimetic can also incorporate any amount of natural amino acid conservative substitutions as long as such substitutions also do not substantially alter the mimetic's structure and/or inhibitory or binding activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

The term "specific binding" refers to binding between two molecules, for example, a ligand and a receptor, characterized by the ability of a molecule (ligand) to associate with another specific molecule (receptor) even in the presence of many other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

Statistically significant refers to a p-value that is <0.05, preferably <0.01 and most preferably <0.001.

"Patient" refers to humans, domesticated animals (e.g., cats, dogs), farm animals (e.g., chickens, cows, sheep, horses, pigs), and laboratory animals (e.g., rats, mice).

The term antibody is used to include intact antibodies and binding fragments thereof. Typically, fragments compete with the intact antibody from which they were derived and with other antibodies for specific binding to an antigen.

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity. The term includes an organic or inorganic chemical such a peptide, including antibodies, proteins and small molecules (less than 500 D) and natural products.

The term "symptom" or "clinical symptom" includes subjective evidence of a disease, such as an aura, as perceived by the patient, as well as objective evidence of a disease as observed by a physician, e.g., epileptic neurological activity.

DETAILED DESCRIPTION OF THE INVENTION

I. General

A surprising discovery has been made that inhibitors of binding of PDZ proteins to one or more PLs are therapeutic in epilepsy. For example, such inhibitors can reduce neuronal damage caused by epilepsy. The inhibitor can be an inhibitor of PSD-95 binding to a PL. In an aspect, the inhibitor is effective to reduce neuronal cell death that occurs after an episode of epilepsy (e.g., a seizure).

The invention provides agents useful for treating or effecting prophylaxis of symptoms of epilepsy. The invention is based in part on results described in the examples in which a PSD-95 antagonist that disrupts specific binding of PSD-95 to NMDAR 2B was found to reduce epilepsy in a rat model of this disorder. Epilepsy differs from other diseases in which it has been proposed that such antagonists would be useful in that epilepsy is not known to be the result of excitotoxicity. Although an understanding of mechanism is not required for practice of the invention, it is believed that such agents of the invention act at least in part by inhibiting interaction between NMDARs (particularly NR2A, 2B, 2C and D) with postsynaptic density 95 protein (i.e., PSD-95 inhibitors). The agents may also inhibit interactions between PSD-95 and nNOS (GenBank NM_008712). The agents may also inhibit interactions of PSD-95 family members SAP102 (Muller, Neuron 17, 255-265 (1996)), SAP97 (GenBank NM_007862), and PSD93 (GenBank NM_0011807), as well as the PDZ-containing protein TIP1 (GenBank NM_029564). Other inhibitors that can be used are disclosed in Applicants' copending U.S. application Ser. No. 12/040,851, filed Feb. 29, 2008, and 60/947,883, filed Jul. 3, 2007, both incorporated by reference in their entirety. Any suitable combination or derivative of the inhibitors mentioned or incorporated by reference herein can also be used. Although the methods of the invention can be used for any form of epilepsy, they are particularly useful when administered after an episode of epilepsy.

II. Agents

Agents include chimeric peptides and peptidomimetics having at least two components. The first component is an active peptide, which optionally has an amino acid sequence including or based on the PL motif of a NMDA Receptor (i.e., a PL peptide) or PDZ domain of PSD-95. Active peptides useful in the invention inhibit interaction between PDZ domains 1 and 2 of post synaptic density protein 95 (PSD-95) (human amino acid sequence provided by Stathakism, Genomics 44(1):71-82 (1997)) and the C-terminal PL sequence of one or more NMDA Receptor 2 subunits including the NR2B subunit of the neuronal N-methyl-D-aspartate receptor (Mandich et al., Genomics 22, 216-8 (1994)). NMDAR2B has GenBank ID 4099612, a C-terminal 20 amino acids FNGSSNGHVYEKLSSIESDV (SEQ ID NO:12) and a PL motif ESDV (SEQ ID NO:1). However, inhibition can also be shown from species variants of the proteins. A list of NMDA and glutamate receptors that can be used appears below:

TABLE 1

NMDA RECEPTORS WITH PL SEQUENCES

| Name | GI or Acc# | C-terminal 20mer sequence | C-terminal 4mer sequence | PL |
|---|---|---|---|---|
| NMDAR1 | 307302 | HPTDITGPLNLSDPSVSTVV (SEQ ID NO: 13) | STVV (SEQ ID NO: 14) | X |
| NMDAR1-1 | 292282 | HPTDITGPLNLSDPSVSTVV (SEQ ID NO: 13) | STVV (SEQ ID NO: 14) | X |
| NMDAR1-4 | 472845 | HPTDITGPLNLSDPSVSTVV (SEQ ID NO: 13) | STVV (SEQ ID NO: 14) | X |
| NMDAR1-3b | 2343286 | HPTDITGPLNLSDPSVSTVV (SEQ ID NO: 13) | STVV (SEQ ID NO: 14) | X |
| NMDAR1-4b | 2343288 | HPTDITGPLNLSDPSVSTVV (SEQ ID NO: 13) | STVV (SEQ ID NO: 14) | X |
| NMDAR1-2 | 11038634 | RRAIEREEGQLQLCSRHRES (SEQ ID NO: 15) | HRES (SEQ ID NO: 16) | |
| NMDAR1-3 | 11038636 | RRAIEREEGQLQLCSRHRES (SEQ ID NO: 15) | HRES (SEQ ID NO: 16) | |
| NMDAR2C | 6006004 | TQGFPGPCTWRRISSLESEV (SEQ ID NO: 17) | ESEV (SEQ ID NO: 2) | X |
| NMDAR3 | 560546 | FNGSSNGHVYEKLSSIESDV (SEQ ID NO: 12) | ESDV (SEQ ID NO: 1) | X |
| NMDAR3A | 17530176 | AVSRKTELEEYQRTSRTCES (SEQ ID NO: 18) | TCES (SEQ ID NO: 19) | |
| NMDAR2B | 4099612 | FNGSSNGHVYEKLSSIESDV (SEQ ID NO: 12) | ESDV (SEQ ID NO: 1) | X |
| NMDAR2A | 558748 | LNSCSNRRVYKKMPSIESDV (SEQ ID NO: 20) | ESDV (SEQ ID NO: 1) | X |
| NMDAR2D | 4504130 | GGDLGTRRGSAHFSSLESEV (SEQ ID NO: 21) | ESEV (SEQ ID NO: 2) | X |
| Glutamate receptor delta 2 | AF009014 | QPTPTLGLNLGNDPDRGTSI (SEQ ID NO: 22) | GTSI (SEQ ID NO: 23) | X |
| Glutamate receptor 1 | I28953 | MQSIPCMSHSSGMPLGATGL (SEQ ID NO: 24) | ATGL (SEQ ID NO: 25) | X |
| Glutamate receptor 2 | L20814 | QNFATYKEGYNVYGIESVKI (SEQ ID NO: 26) | SVKI (SEQ ID NO: 27) | X |

TABLE 1-continued

NMDA RECEPTORS WITH PL SEQUENCES

| Name | GI or Acc# | C-terminal 20mer sequence | C-terminal 4mer sequence | PL |
|---|---|---|---|---|
| Glutamate receptor 3 | AF167332 | QNYATYREGYNVYGTESVKI (SEQ ID NO: 28) | SVKI (SEQ ID NO: 27) | X |
| Glutamate receptor 4 | U16129 | HTGTAIRQSSGLAVIASDLP (SEQ ID NO: 29) | SDLP (SEQ ID NO: 30) | |
| Glutamate receptor 5 | U16125 | SFTSILTCHQRRTQRKETVA (SEQ ID NO: 31) | ETVA (SEQ ID NO: 32) | X |
| Glutamate receptor 6 | U16126 | EVINMHTFNDRRLPGKETMA (SEQ ID NO: 33) | ETMA (SEQ ID NO: 34) | X |
| Glutamate receptor 7 | U16127 | RRLPGKDSMACSTSLAPVFP (SEQ ID NO: 35) | PVFP (SEQ ID NO: 36) | |

Some active peptides inhibit interactions between PSD-95 and multiple NMDAR subunits. In such instances, use of the peptide does not necessarily require an understanding of the respective contributions of the different NMDARs to excitatory neurotransmission. Other active peptides are specific for a single NMDAR.

Active peptides include or are based on a PL motif from the C-terminus of any of the above subunits and have an amino acid sequence comprising [S/T]-X-[V/L]. This sequence preferably occurs at the C-terminus of the peptides of the invention. Preferred peptides have an amino acid sequence comprising [E/D/N/Q]-[S/T]-[D/E/Q/N]-[V/L] at their C-terminus. Exemplary peptides comprise: ESDV (SEQ ID NO:1), ESEV (SEQ ID NO:2), ESTV (SEQ ID NO:37), ETDV (SEQ ID NO:3), ETEV (SEQ ID NO:4), DTDV (SEQ ID NO:5), and DTEV (SEQ ID NO:6) as the C-terminal amino acids. Two particularly preferred peptides are KLSSIESDV (SEQ ID NO:9), and KLSSIETDV (SEQ ID NO:7). Peptides of the invention without an internalization peptide usually have 3-25 amino acids, peptide lengths (also without an internalization peptide) of 5-10 amino acids, and particularly 9 amino acids are preferred. In some such active peptides, all amino acids are from the C-terminus of an NMDA receptor.

Other active peptides include PDZ domain 1 and/or 2 of PSD-95 or a subfragment of any of these that inhibits interactions between PSD-95 and an NMDA receptor, such as NMDA 2B. Such active peptides comprise at least 50, 60, 70, 80 or 90 amino acids from PDZ domain 1 and/or PDZ domain 2 of PSD-95, which occur within approximately amino acids 65-248 of PSD-95 provided by Stathakism, Genomics 44(1): 71-82 (1997) (human sequence) or NP_031890.1, GI:6681195 (mouse sequence) or corresponding regions of other species variants.

Any of the peptides of the invention can be linked, preferably at its N-terminus, to an internalization peptide that facilitates translocation through the plasma membrane of a cell. Examples of these peptide include tat derived from HIV (Vives et al., 1997, J. Biol. Chem. 272:16010; Nagahara et al., 1998, Nat. Med. 4:1449), antennapedia from Drosophila (Derossi et al., 1994, J. Biol. Chem. 261:10444), VP22 from herpes simplex virus (Elliot and D'Hare, 1997, Cell 88:223-233), complementarity-determining regions (CDR) 2 and 3 of anti-DNA antibodies (Avrameas et al., 1998, Proc. Natl. Acad. Sci. U.S.A., 95:5601-5606), 70 KDa heat shock protein (Fujihara, 1999, EMBO J. 18:411-419) and transportan (Pooga et al., 1998, FASEB J. 12:67-77). For example, the HIV TAT internalization peptide YGRKKRRQRRR (SEQ ID NO:38) can be used. Two preferred peptides including this HIV Tat internalization peptide and an active peptide are YGRKKRRQRRRKLSSIETDV (SEQ ID NO:8, Tat-NR2B9c$_{(TDV)}$), and YGRKKRRQRRRKLSSIESDV (SEQ ID NO:10, Tat-NR2B9c$_{(SDV)}$).

Variants of the standard tat sequence YGRKKRRQRRR (SEQ ID NO:38) can also be used. Co-pending application 60/904,507, filed Mar. 2, 2007 reports that the standard tat peptide binds to and inhibits N-type calcium channels, which binding may lead to a variety of side effects. Although practice of the invention is not dependent on an understanding of mechanism, it is believed that both capacity to cross membranes and binding to N-type calcium channels of tat are conferred by the unusually high occurrence of positively charged residues Y, R and K in the peptide. Variant peptides for use in the invention should retain ability to facilitate uptake into cells but have reduced capacity to bind N-type calcium channels. Some suitable internalization peptides comprise or consist of an amino acid sequence XGRKKRRQRRR (SEQ ID NO:39), in which X is an amino acid other than Y. A preferred tat variant has the N-terminal Y residue substituted with F. Thus, a tat variant comprising or consisting of FGRKKRRQRRR (SEQ ID NO:40) is preferred. Another preferred variant tat internalization peptide consists of GRKKRRQRRR (SEQ ID NO:41). If additional residues flanking XGRKKRRQRRR (SEQ ID NO:39) are present (beside the active peptide) the residues can be for example, natural amino acids flanking this segment from a tat protein, spacer or linker amino acids of a kind typically used to join two peptide domains, e.g., Gly (Ser)$_4$ (SEQ ID NO:42), TGEKP (SEQ ID NO:43), GGRRGGGS (SEQ ID NO:44), or LRQRDGERP (SEQ ID NO:45) (see, e.g., Tang et al. (1996), J. Biol. Chem. 271, 15682-15686; Hennecke et al. (1998), Protein Eng. 11, 405-410)), or can be any other amino acids that do not detectably reduce capacity to confer uptake of the variant without the flanking residues and do not significantly increase inhibition of N-type calcium channels relative to the variant without the flanking residues. Preferably, the number of flanking amino acids other than an active peptide does not exceed ten on either side of XGRKKRRQRRR (SEQ ID NO:39). Preferably, no flanking amino acids are present, and the internalization peptide is linked at its C-terminus directly to an active peptide.

Other tat variants that can be used to allow uptake of any of the active peptides of the invention for inhibition of PSD-95 interactions without inhibiting N-type calcium channels include those presented in Table 2 below. It is recommended that these internalization peptides be screened to confirm desired uptake and lack of inhibition of N-type calcium channels. These sequences are predicted herein to maintain transport capability without inhibiting N-type calcium channels and thus allow a greater therapeutic index for the treatment of epilepsy.

TABLE 2

| | | |
|---|---|---|
| X-FGRKKRRQRRRKLSSIESDV | (F-TatNR2B9c$_{(SDV)}$; SEQ ID NOS: 46-48) | |
| X-GKKKKKQKKKKLSSIESDV | (SEQ ID NOS: 49-51) | |
| X-RKKRRQRRRKLSSIESDV | (SEQ ID NOS: 52-54) | |
| X-GAKKRRQRRRKLSSIESDV | (SEQ ID NOS: 55-57) | |
| X-AKKRRQRRRKLSSIESDV | (SEQ ID NOS: 58-60) | |
| X-GRKARRQRRRKLSSIESDV | (SEQ ID NOS: 61-63) | |
| X-RKARRQRRRKLSSIESDV | (SEQ ID NOS: 64-66) | |
| X-GRKKARQRRRKLSSIESDV | (SEQ ID NOS: 67-69) | |
| X-RKKARQRRRKLSSIESDV | (SEQ ID NOS: 70-72) | |
| X-GRKKRRQARRKLSSIESDV | (SEQ ID NOS: 73-75) | |
| X-RKKRRQARRKLSSIESDV | (SEQ ID NOS: 76-78) | |
| X-GRKKRRQRARKLSSIESDV | (SEQ ID NOS: 79-81) | |
| X-RKKRRQRARKLSSIESDV | (SEQ ID NOS: 82-84) | |
| X-RRPRRPRRPRRKLSSIESDV | (SEQ ID NOS: 85-87) | |
| X-RRARRARRARRKLSSIESDV | (SEQ ID NOS: 88-90) | |
| X-RRRARRRARRKLSSIESDV | (SEQ ID NOS: 91-93) | |
| X-RRRPRRRPRRKLSSIESDV | (SEQ ID NOS: 94-96) | |
| X-RRPRRPRRKLSSIESDV | (SEQ ID NOS: 97-99) | |
| X-RRARRARRKLSSIESDV | (SEQ ID NOS: 100-102) | |

X can represent a free amino terminus, a biotin molecule or other capping moiety including, but not limited to, H, acetyl, benzoyl, alkyl group (aliphatic), pyroglutamate, alkyl group with cycloalkyl group at the end, biotin with alkyl spacer, or 5,6-carboxyfluorescein (5,6-FAM). Chemical coupling of the capping group to the N-terminal peptide can be through an amide chemistry, sulphamide chemistry, sulphone chemistry, alkylation chemistry. In addition, X can also be an amino acid other that tyrosine.

Internalization peptides are usually linked to active peptides as fusion peptides, but can also be joined by chemical linkage. Coupling of the two constituents can be accomplished via a coupling or conjugating agent. Numerous such agents are commercially available and are reviewed by S. S. Wong, Chemistry of Protein Conjugation and Cross-Linking, CRC Press (1991). Some examples of cross-linking reagents include J-succinimidyl 3-(2-pyridyldithio) propionate (SPDP) or N,N'-(1,3-phenylene) bismaleimide; N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents include p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Peptides of the invention, optionally fused to internalization domains, can be synthesized by solid phase synthesis or recombinant methods. Peptidomimetics can be synthesized using a variety of procedures and methodologies described in the scientific and patent literature, e.g., Organic Syntheses Collective Volumes, Gilman et al. (Eds) John Wiley & Sons, Inc., NY, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; Ostresh (1996) *Methods Enzymol.* 267:220-234.

Peptides of the invention without an internalization peptide usually have 3-25 amino acids, Peptide lengths (also without an internalization peptide) of 5-10 amino acids, and particularly 9 amino acids are preferred.

Appropriate pharmacological activity of peptides or peptidomimetics can be confirmed, if desired, using the animal model described herein. Optionally, peptides or peptidomimetics can also be screened for capacity to inhibit interactions between PSD-95 and NMDAR 2B using assays described in e.g., US 20050059597, which is incorporated by reference. Useful peptides typically have IC50 values of less than 50 uM, 25 µM, 10 uM, 0.1 µM or 0.01 µM in such an assay. Preferred peptides typically have an IC50 value of between 0.001-1 µM, and more preferably 0.05-0.5 or 0.05 to 0.1 µM Peptides such as those just described can optionally be derivatized (e.g., acetylated, phosphorylated and/or glycosylated) to improve the binding affinity of the inhibitor, to improve the ability of the inhibitor to be transported across a cell membrane or to improve stability. As a specific example, for inhibitors in which the third residue from the C-terminus is S or T, this residue can be phosphorylated before use of the peptide.

Agents also include small molecules that inhibit interactions between PSD-95 and NMDAR 2B, and/or other interactions described above. Suitable small-molecule inhibitors are described in co-pending International Application No. PCT/US2006/062715, which was filed on 29 Dec. 2005, herein incorporated by reference in its entirety. These molecules were identified by in silico screening of a compound library for binding to PSD-95, and binding of exemplary compounds was verified experimentally. Suitable compounds include compounds having the general structure of $P_0$-A-B—C-D-E, where D and E are optional, and $P_0$ is:

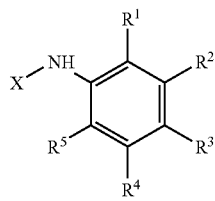

wherein one of $R^1$, $R^2$, $R^3$, $R^4$, and $R^5$ is COOH, and wherein the remainder of $R^1$, $R^2$, $R^3$, $R^4$, and $R^5$ are selected from the group consisting of F, H, $OCH_3$ and $CH_3$; and X is -A-B—C-D-E, wherein A, B, C, D and E are connected through single bonds and A is selected from the group consisting of C=O, NH, $SO_2$ and $(CH_2)_m$, wherein m=0, 1, 2, 3, 4, or 5;

B is:

—$OCH_2$—, C=O,

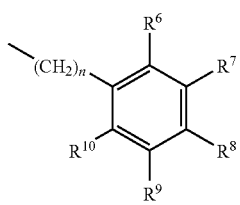

wherein one of $R^6$-$R^{10}$ is bonded to —C-D-E, and wherein the remainder of $R^6$-$R^{10}$ are selected from the group of H, OH, F, Cl, Br, I, $CH_3$, $CH_2CH_3$ and $OCH_3$, and n=0 or 1; or a ring system selected from the group consisting of saturated or unsaturated cycloalkyl or heterocycle; or

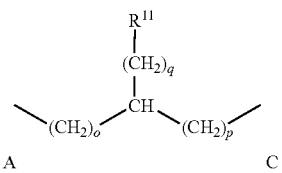

wherein o and p=0 or 1, q=0, 1, 2, 3 or 4, and $R^{11}$ is selected from the group consisting of substituted or unsubstituted lower alkyl, amide, thioether, phenyl, phenol, indole, imidazole, $NH(NH_2)(N(+)H_2)$, COOH, SH, OH, or H;

C is selected from the group consisting of —O—, C=O, NH, CONH, S, phthalamide, $CH_3$, H, $SO_2$ and $(CH_2)_r$, wherein r=0, 1, 2, 3, 4, or 5;

D is optional and when C is not terminating, D is selected from the group consisting of —CN—, C=O, NH, S, O, $SO_2$, $(CH_2)_s$, wherein s=0, 1, 2, 3, 4, or 5, and $(CH_2)_t$—OH, wherein t=0, 1, 2, 3, 4 or 5, and

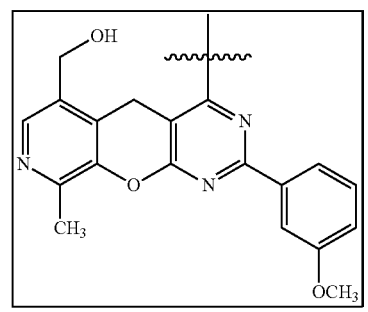

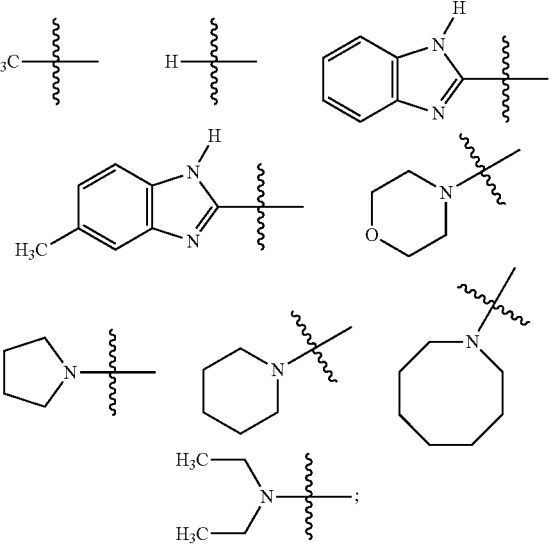

and

E is optional and when D is not terminating, E is cyclohexyl or phenyl, either substituted with lower alkyl, lower alkoxy, ketone, OH, COOH, nitroso, N-substituted indoline, or a cell membrane translocation peptide; or —$(CH_2)_u$—$(CHR^{12}R^{13})$, wherein u=0, 1, 2, 3, 4, 5, 6, 7, 8, 9, 10, 11, 12, 13, 14, 15, 16, or 17 and $R^{12}$ and $R^{13}$ are independently selected from the group consisting of H, OH, cyclohexane, cyclopentane, phenyl, substituted phenyl, cyclopentadiene; or branched lower alkyl including isopropyl, isobutyl, 1-isopropyl-2-methyl-butyl, 1-ethyl-propyl; or —NH—$COR^{14}$, wherein $R^{14}$ is $(CR^{15}R^{16})_vH$, wherein v=0, 1, 2, 3, 4, 5, 6, 7, 8, 9, 10, 11, 12, 13, 14, 15, 16, or 17 and $R^{15}$ and $R^{16}$ independently selected from the group consisting of H, cyclohexane, phenyl, and a cell membrane translocation peptide.

Alternatively, $P_0$ is:

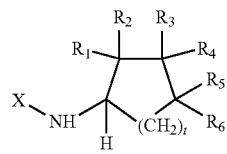

wherein t=0, 1 or 2, either $R^1$, $R^2$, $R^3$, $R^4$, $R^5$ or $R^6$ are COOH, and the remainder of $R^1$, $R^2$, $R^3$, $R^4$, $R^5$ and $R^6$ are selected from the group consisting of H, $CH_3$, F, and $OCH_3$, and X is A-B—C-D-E, wherein A, B, C, D and E are connected through single bonds and A is selected from the group consisting of C=O, $SO_2$, NH, and $(CH_2)_m$, wherein m=0, 1, 2, 3, 4, or 5;

B is:

—OCH$_2$—, C=O; or

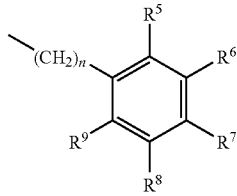

wherein one of R$^5$-R$^9$ is bonded to —C-D-E, and wherein the remainder of R$^5$-R$^9$ are selected from the group of H, OH, F, Cl, Br, I, CH$_3$, CH$_2$CH$_3$ and OCH$_3$, and n=0 or 1; or a ring system selected from the group consisting of saturated or unsaturated cycloalkyl or heterocycle; or

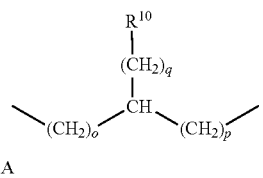

wherein o and p=0 or 1, and R$^{10}$ is selected from the group consisting of substituted or unsubstituted alkyl, amide, thioether, phenyl, phenol, indole, imidazole, NH(NH$_2$)(N(+)H$_2$), COOH, SH, OH, or H;

C is selected from the group consisting of C=O, NH, S, phthalamide, —O—, CH$_3$, H, SO$_2$, and (CH$_2$)$_r$, wherein r=0, 1, 2, 3, 4, or 5;

D is optional and when C is not terminating, D is selected from the group consisting of C=O, —CN—, NH, S, O, SO$_2$, (CH$_2$)$_s$, wherein s=0, 1, 2, 3, 4, or 5, and

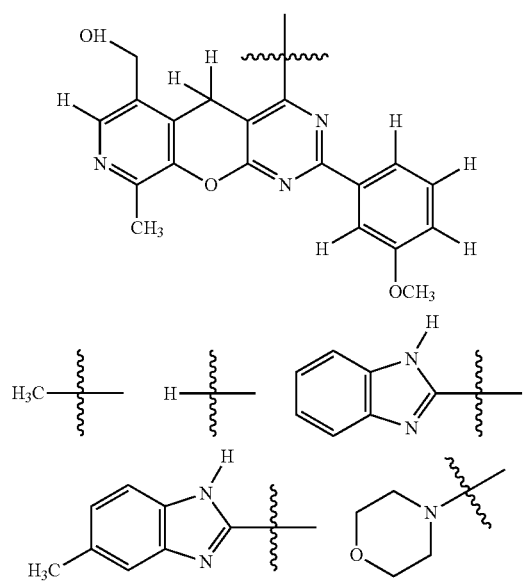

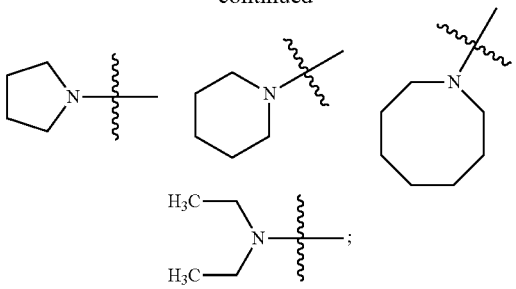

and

E is phenyl or cyclohexyl, either substituted with lower alkyl, lower alkoxy, ketone, OH, COOH, nitroso, N-substituted indoline; or —(CHR$^{11}$R$^{12}$)$_u$, wherein u=0, 1, 2, 3, 4, 5, 6, 7, 8, 9, 10, 11, 12, 13, 14, 15, 16, or 17 and R$^{11}$ and R$^{12}$ are independently selected from the group consisting of H, OH, cyclohexane, cyclopentane, phenyl, substituted phenyl, cyclopentadiene; or branched lower alkyl including isopropyl, isobutyl, 1-isopropyl-2-methyl-butyl, 1-ethyl-propyl; or —NH—COR$^{11}$, wherein R$^{11}$ is (CHR$^{12}$R$^{13}$)$_s$, wherein s=0, 1, 2, 3, 4, 5, 6, 7, 8, 9, 10, 11, 12, 13, 14, 15, 16, or 17 and R$^{12}$ and R$^{13}$ independently selected from the group consisting of H, cyclohexane, phenyl, and a cell membrane translocation peptide.

Some preferred compounds have the following structure:

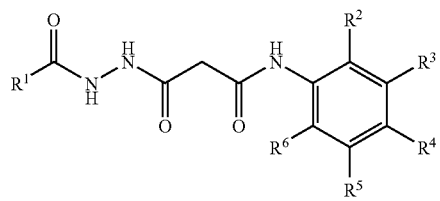

wherein R$^1$ is a member selected from the group consisting of cyclohexyl substituted with 0-4 R$^7$, phenyl substituted with 0-4 R$^7$, —(CH$_2$)$_u$—(CHR$^8$R$^9$), a branched C$_{1-6}$ alkyl (isopropyl, isobutyl, 1-isopropyl-2-methyl-butyl, 1-ethyl-propyl), and —NH—C(O)—(CR$^{10}$R$^{11}$)$_v$H;

each R$^7$ is independently a member selected from the group consisting of C$_{1-6}$ alkyl, C$_{1-6}$ alkoxy, —C(O)R$^{12}$, OH, COOH, —NO, N-substituted indoline and a cell membrane translocation peptide each R$^8$ and R$^9$ is independently selected from the group consisting of H, OH, cyclohexane, cyclopentane, phenyl, substituted phenyl (for instance, substituted with halo, alkyl and/or hydroxyl groups) and cyclopentadiene;

each R$^{10}$ and R$^{11}$ is independently selected from the group consisting of H, cyclohexane, phenyl and a cell membrane translocation peptide;

R$^{12}$ is a member selected from the group consisting of C$_{1-6}$ alkyl and aryl; and each of u and v are independently from 0 to 20;
wherein one of R$^2$, R$^3$, R$^4$, R$^5$ and R$^6$ is —COOH, and wherein the remainder of R$^2$, R$^3$, R$^4$, R$^5$ and R$^6$ are each independently selected from the group consisting of F, H, OCH$_3$ and CH$_3$.

In one embodiment R$^1$ is —(CH$_2$)$_u$—(CHR$^8$R$^9$). In another embodiment, R$^1$ is a member of the above-defined group of R$^1$ substituents other than —(CH$_2$)$_u$—(CHR$^8$R$^9$).

A preferred agent has the following structure

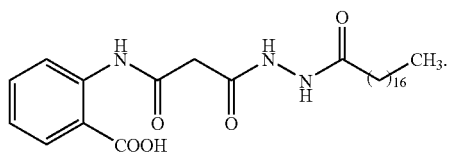

0620-0057

Other compounds can be screened from naturally occurring or synthetic molecules. Agents to be screened can also obtained from natural sources, such as, e.g., marine microorganisms, algae, plants, fungi, Random libraries of peptides or other compounds can also be screened for binding to PSD-95 and capacity to inhibit interactions of PSD-95 with the NMDARs and/or the molecules described in section I above. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. Avimers constituting multimers of A-domains can be used in similar fashion to antibodies (Silverman et al. Nat. Biotechnol. 23, 1493-4 (2005)). Compounds with the binding and inhibitory properties described above can be further screened in an animal model of epilepsy.

Optionally, any of the above compounds is mixed with a pharmaceutical excipient as a pharmaceutical composition.

III. Epilepsy

Epilepsy is a CNS disorder characterized by recurring, unprovoked events of uncontrolled electrical activity in the brain, generally in the form of excessive and/or synchronous neural activity. Epilepsy is a group of syndromes all involving episodic abnormal electrical activity in the brain. The recurring epileptic episodes can occur from very rarely (e.g., not for many years) to very frequently (e.g., multiple times a day). Many individuals are asymptomatic between episodes. Generally speaking, most epileptic seizures are spontaneous (happen without a known trigger or cause), sudden (happening without an advance indication), short-lived (lasting a few seconds or minutes), and self-limited (ceasing without medical help).

General Symptoms of Epilepsy

Almost any type of behavior that happens repetitively may indicate an epileptic seizure, including convulsions, muscle spasms, loss of consciousness, strange sensations, emotions and/or behavior. Any one or more of the following symptoms can indicate epilepsy. dizziness; fainting; confusion; memory loss; headache; changes in mood or energy level; a convulsion with or without a fever; periods of blackout or confused memory; occasional spells in which bladder or bowel control is lost, followed by extreme fatigue; episodes of blank staring; brief periods of no response to questions or instructions; sudden stiffening or falls for no apparent reason; episodes of blinking or chewing at inappropriate times; dazed behavior; being unable to talk or communicate for a short time; repeated movements that look out of place or unnatural; sudden fear, anger or panic for no reason; odd changes in the way things look, sound, smell or feel; muscle jerks of arms, legs or body; and/or clusters of swift jerking movements in babies.

Different Types of Classification of Epilepsies

Epilepsies can be classified by many different criteria, including: (1) the first cause (or etiology); (2) the observable manifestations of the seizures, known as semiology; (3) the location in the brain where the seizures originate; (4) as a part of discrete, identifiable medical syndromes; and (5) the event that triggers the seizures, if any. The 1981 classification scheme by International League Against Epilepsy (ILAE) remains in common use and is based on observation (based on clinical and electrophysiologic data) rather than the underlying pathophysiology or anatomy. In 1989, the ILAE proposed a classification scheme for epilepsies and epileptic syndromes which can be regarded as a two-axis scheme having the cause on one axis and the extent of localisation within the brain on the other. Since 1997, the ILAE have been working on a new scheme that has five axes: ictal phenomenon, seizure type, syndrome, etiology and impairment. Of course, many cases of epilepsy remain in an "undetermined" group because their syptoms are not limited to thos of any single classification.

Classifications Based on Localization of Epileptic Seizures

An epileptic seizure involves epileptic activity of neurons (typically excessive and/or hypersynchronous, and usually self-limited activity) in the brain. The International Classification of Epileptic Seizures broadly divides epileptic seizures into focal (also called partial) and generalized epileptic seizures. A partial seizure is typically a seizure whose initial semiology indicates, or is consistent with, initial activation of only part of one cerebral hemisphere. A generalized seizure is typically a seizure whose initial semiology indicates, or is consistent with, more than minimal involvement of both cerebral hemispheres. A partial seizure may spread within the brain, a process known as secondary generalization.

Partial seizures are further classified on the extent to which consciousness is affected. If it is unaffected, then it is a simple partial seizure that often involves a relatively small area of the brain such as the frontal, temporal, occipital or parietal lobe.

The symptoms of seizure manifested by an individual can be indicative of the part of brain in which the underlying abnormal neural activity originates. By way of example, retention of conciousness, optionally combined with localized or whole body muscle spasms, twitches, tics and/or hallucinations, can indicate focal epilepsy. Temporal lobe SPS symptoms can include: an "epigastric rising sensation" déjà vu or jamais vu, a flashback of memory, a sudden, intense feeling of fear or joy and/or a strange taste or smell, sudden behavior changes, unusual behavior, aggression, anger, or agitation. Frontal lobe SPS can be associated with strange movements, stiffness or jerking that can be initially localized to one part of the body but can spread to others. Parietal lobe SPS can include strange sensations such as numbness or tingling, burning sensations or a feeling of heat and/or a feeling that part of the body, is bigger or smaller than they really are. Occipital lobe SPS can involve visual sensations, such as: distortion or loss of vision, seeing flashing lights or coloured shapes and/or hallucination.

A complex partial (psychomotor) seizure generally involves impaired awareness (with the individual being only partly conscious), impaired responsiveness and impaired memory of most or all of the seizure. Temporal lobe CPS is often manifested by automatisms or looking from side to side in a confused way. This type of CPS usually lasts around 2-3 minutes (about the length of a song on the radio) and then it takes the person 5-10 minutes to fully regain normal function. In contrast, frontal lobe CPS is often much shorter then temporal lobe CPS, usually lasting about 15-30 seconds, often characterized by limbic movements, followed by a quick recovery.

Generalized seizures are divided according to the effect on the body but generally involve loss of consciousness. These include absence (petit mal), myoclonic, clonic, tonic, tonic-clonic (grand mal) and atonic seizures. Generalized seizures are classified predominantly on the basis of their motor manifestations.

Classification Based on Symptomology:

An epileptic seizure can be accompanied by a charateristic motor event that can comprise an increase (positive) or decrease (negative) in muscle contraction to produce a movement. Epileptic seizures can classified in terms of the accompanying motor manifestations as follows:

1) Tonic: A sustained increase in muscle contraction lasting a few seconds to minutes
2) Epileptic spasm: a sudden flexion, extension or mixed extension-flexion of predominantly proximal and truncal muscles which is usually more sustained than a myoclonic movement but not as sustained as a tonic seizure, i.e., about 1 sec. Limited forms may occur: grimacing, head nodding. Epileptic spasms frequently occur in clusters.
3) Dystonic: Sustained contractions of both agonist and antagonist muscles producing athetoid or twisting movements which when prolonged may produce abnormal postures.
4) Myoclonic: Sudden, brief (<100 msec) involuntary single or multiple contraction(s) of muscles(s) or muscle groups of variable topography (axial, proximal limb, distal).
5) Negative myoclonic: Interruption of tonic muscular activity for <500 msec without evidence of antecedent myoclonia.
6) Clonic: Myoclonus which is regularly repetitive, involves the same muscle groups, at a frequency of about 2-3 c/sec, and is prolonged.
7) Tonic-clonic: A sequence consisting of a tonic followed by a clonic phase. Variants such as clonic-tonic-clonic may be seen.
8) Generalised tonic-clonic seizure (also called bilateral tonic-clonic seizure, formerly "Grand Mal" Seizure)): Bilateral symmetrical tonic contraction then bilateral clonic contractions of somatic muscles usually associated with autonomic phenomena.
9) Atonic: Sudden loss or diminution of muscle tone without an apparent preceding myoclonic or tonic event lasting one to two seconds or more.

Seizures that are not manifested by obvious motor events are sometimes classified on the basis of other experienced symptoms. "Absence" seizures are typically brief seizures where the individual loses awareness, for example by going blank and staring. The seizures can be quite subtle and hard to see, as there may be no obvious movement. Absences tend to be more frequent in children (up to hundreds of seizures a day), but can also happen in adults. Some children can have hundreds of absences every day. "Atypical" absence seizures last longer than a few seconds and can involve some movement of the body, such as jerking of the shoulders.

Sensory seizures include perceptual experience not caused by appropriate stimuli in the external world. An "aura" constitutes a subjective ictal phenomenon that, in a given patient, may precede an observable symptom of seizure. If alone, it constitutes a sensory seizure. An autonomic aura comprises a sensation consistent with involvement of the autonomic nervous system, including cardiovascular, gastrointestinal, sudomotor, vasomotor and thermoregulatory functions. An autonomic seizure typically comprises an objectively documented and distinct alteration of autonomic nervous system function, for example involving cardiovascular, pupillary, gastrointestinal, sudomotor, vasomotor and thermoregularity functions.

Classification Based on Etiology

Based on the underlying cause, epilepsies can be divided into idiopathic (i.e., no apparent underlying cause), symptomatic and cryptogenic types. Cryptogenic epilepsy is epilepsy suspected of having a specific underlying cause, which has not been identified as yet. Symptomatic epilepsy is caused by known structural abnormalities or damage in the brain or by an underlying disease, such as congenital brain malformation, injury or trauma (at birth or later), lack of oxygen to the brain causing damage, infection with permanent damage, tumour, tangle of blood vessels, stroke, and/or metabolic disorder.

Status Epilepticus (SE)

Although many epileptic seizures are infrequent and of short duration (e.g., under a few minutes), in some instances an individual can suffer status epilepticus, characterized by a continuing seizure lasting longer than epileptic seizures generally do, for example at least about 5, 10, or 30 minutes. Status epilepticus can also occur in the form of two or more recurrent seizures between which the individual does not return to baseline consciousness. The seizure(s) can be generalized and/or convulsive; prolonged convulsions with impaired consciousness constitutes generalized convulsive SE (GCSE). Although a patient with convulsions is easily recognized, some patients who have been in GCSE may progress to have minimal or no apparent motor activity but still show seizures on an electroencephalograph (EEG). An individual with nonconvulsive SE (NCSE) can exhibit a wide variety of clinical manifestation including coma, confusion, somnolence, altered affect, fugue states, aphasia, abnormal autonomic/vegetative symptoms, delusions, hallucinations, and paranoia. NCSE can be divided into either generalized (absence), focal (complex partial), or other. The 'epileptic twilight state', during which there is intact arousal with impairment of attention, can represent the clinical overlap between generalized and focal NCSE. Simple partial SE is typically indicated by prolonged focal seizures, such as isolated hand jerking, associated with intact consciousness.

Other Common Epileptic Disorders

Some of the more common epileptic disporders and related conditions that can be treated by the agents and methods described herein include one or more the following: benign familial neonatal seizures; early myoclonic encephalopathy; Ohtahara syndrome; Migrating partial seizures of infancy; West syndrome; benign myoclonic epilepsy in infancy; benign familial and non-familial infantile seizures; Dravet's syndrome; HH syndrome; Myoclonic status in nonprogressive encephalopathies; benign childhood epilepsy with centrotemporal spikes; early onset benign childhood occipital epilepsy (Panayiotopoulos type); late onset childhood occipital epilepsy (Gastaut type); epilepsy with myoclonic absences; epilepsy with myoclonic-astatic seizures; Lennox-Gastaut syndrome; Landau-Kleffner syndrome; epilepsy with continuous spike-and-waves during slow-wave sleep (other than LKS); childhood absence epilepsy; progressive myoclonus epilepsies; idiopathic generalized epilepsies with variable phenotypes such as juvenile absence epilepsy or juvenile myoclonic epilepsy or epilepsy with generalized tonic-clonic seizures only; reflex epilepsies; idiopathic photosensitive occipital lobe epilepsy; other visual sensitive epilepsies; primary reading epilepsy; startle epilepsy; autosomal dominant nocturnal frontal lobe epilepsy; familial temporal lobe epilepsies; generalized epilepsies with febrile seizures plus; familial focal epilepsy with variable foci; symptomatic (or probably symptomatic) focal epilepsies; limbic epilepsies; mesial temporal lobe epilepsy with hippocampal sclerosis; mesial temporal lobe epilepsy defined by specific etiologies; other types defined by location and etiology; neocortical epilepsies; and/or Rasmussen syndrome.

Temporal lobe epilepsy (TLE) is the most common and drug resistant type of adult focal epilepsy. TLE, as a whole, constitutes a common type of epilepsy. The exact incidence is not clear but it is suspected to make up a significant proportion of medication-resistant epilepsy. Approximately 30% (of the 2.7 million cases of epilepsy in the United States) do not adequately respond to medications. Up to a half of these may be due to TLE. Surgically resected hippocampuses from TLE patients reveals hippocampal sclerosis, characterized by gliosis and loss of neurons, as well as axonal sprouting, neurogenesis and synaptogenesis. These features of human TLE are reproduced in the well-established lithium-pilocarpine animal model of TLE. Pilocarpine, a chemoconvulsant, induces an epileptic state that is characterized by continuous seizures, leading to a series of neuropathological changes and subsequent development of spontaneous recurrent seizures (SRS) within 3 to 5 weeks. Extensive cell loss is present in the amygdala, the piriform cortex and the dorsal CA1 hippocampus.

Diagnosis and/or Detection of Epilepsy

Besides the manifestation of observable symptoms, epilepsy can be detected and/or diagnosed by the use of various procedures. These can include electroencephalographyy (EEG), video EEG, computerized tomography (CT) scans, magnetic resonance imaging (MRI), positron emission tomography (PET), and/or single-photon emission computer tomography (SPECT).

EEG is widely used to aid in detection or diagnosis of epilepsy. The presence of interictal epileptiform discharge (IED) can be indicative of epilepsy. Some types of epileptiform phenomena, e.g., a 3- to 7-Hz spike wave discharge, hypsarrhythmia, and/or generalised photoparoxysmal response, are strongly correlated with clinical epilepsy. Focal sharp waves in centro-temporal or occipital regions, or centro-temporal or rolandic EEG discharges, can also be indicative of epilepsy. The location of an epileptogenic zone is relevant: a majority of patients with temporal lobe epilepsy show IED, whereas epileptic foci in mesial or basal cortical regions remote from scalp electrodes are less likely to demonstrate spikes. EEG can optionally be taken at multiple timepoints, during both waking and sleeping. See, e.g., Smith et al., Journal of Neurology Neurosurgery and Psychiatry 2005; 76:ii2-ii7, incorporated by reference in its entirety.

IV. Patients Amenable to Treatment

Patients amenable to treatment include humans having one or more symptoms or disorders of epilepsy including those described above.

Patients amenable to treatment may or may not have other diseases or disorders for which treatment with PSD-95—antagonists has previously been proposed. These diseases and conditions include excitotoxicity mediated diseases, stroke, epilepsy, hypoxia, traumatic injury to the CNS not associated with stroke such as traumatic brain injury and spinal cord injury, Alzheimer's disease and Parkinson's disease. In patients, in which such a comorbid disease is present, the agents of the invention can be effective against epilepsy and the comorbid disease.

Optionally, the agents of the invention are administered to subjects diagnosed with epilepsy that have no history of stroke and/or other disorders mediated by excitotoxicity and/or ischemic brain damage or another disease. The agents of the invention can also be administered to subjects having epilepsy that are not known to be predisposed to, or at increased risk for, a second disease. Optionally the agents of the invention can also be administered to subjects having epilepsy that are known to have a decreased risk for a second disease, or known not to have an increased risk for a second disease. In other situations, the agents of the invention can also be preferentially administered to subjects having epilepsy that have not had a second disease but may be predisposed to, or at increased risk for, a second disease. The agents can also be administered to subjects with an unknown risk of a second disease. The second disease be a PSD-95-mediated disease. Optionally the second disease is stroke, excitotoxicity mediated diseases, stroke, epilepsy, hypoxia, traumatic injury to the CNS not associated with stroke such as traumatic brain injury and spinal cord injury, Alzheimer's disease or Parkinson's disease, congenital brain malformation, infection with permanent damage, CNS tumour, tangle of blood vessels, and/or metabolic disorder.

V. Methods of Treatment, Timing of Administration

The agents of the invention are used to treat patients suffering from, or at risk of developing symptoms of, any symptom of an epileptic disorder, including those described above.

In a preferred method, the agent can be administered at least 30 minutes or one hour after an episode of epilepsy (e.g., a seizure). The agent can be administered for example at least about two, three, four, five, six, eight, ten, twelve, sixteen or twenty four hours after an episode of epilepsy. The agent can also be administered days after the epilepsy episode, e.g., at least about 1, 2, 3, 4, 5, 7, 8, 9, 10 or 12 days after initiation. The agent can also be administered at least a week after the epilepsy episode, e.g., at least about 1, 2 or 3 weeks after the episode.

Optionally, the inhibitor is administered after the epilepsy episode but not later than one or more hours, e.g., not later than about 1, 2, 3, 4, 5, 6, 7, 8, 10, 12, 18 or 24 hours after the episode. Optionally, the inhibitor is administered after the epilepsy episode but not later than one or more days, e.g., not later than about 1, 2, 3, 4, 5, 6, 7, 8, 9, 10, 11, 12, or 14 days after the episode. Optionally, the inhibitor is administered after the epilepsy episode but not later than one or more weeks, e.g., not later than about 1, 1.5, 2, 2.5 or 3 weeks after the episode.

The inhibitor is optionally administered after the epilepsy episode within a time range. The time range can be based on any combination of the timepoints mentioned above. For example, the inhibitor can be administered within a time range of at least about one hour after an episode of epilepsy and not later than about 2 weeks after the episode, such as at least about two hours after an episode of epilepsy and not later than one week after the episode, e.g., at least about three hours after an episode of epilepsy and not later than about three days (or alternatively one week) after the episode.

Optionally, the timing of administration after an episode of epilepsy can be measured from the time of initiation of the episode (e.g., when the episode is short), or from the time of conclusion of an episode (e.g., when an epileptic seizure is of longer duration), or from any timepoint in where signs of epileptic activity in the brain are observed. For the purposes of the invention, the initiation of experienced or observed symptoms of epileptic seizure activity in the brain, not including non-specific seizure premonitions or postictal states, can be regarded as the initiation of the epileptic episode. Likewise, the cessation of experienced or observed symptoms of epileptic seizure activity in the brain can be regarded as the conclusion of the epileptic episode.

Optionally, the agent is not administered before or during an episode of epilepsy. In other instances, the agent can also be administered during an epileptic episode, e.g., a seizure.

If treatment is administered after an episode has started, the treatment is optionally administered at least after about 0.5, 1, 2, 3, 4, 5, 6, 8, 12, 24 or 48 hours after the conclusion of an epileptic seizure. Often a single dose of an agent of the invention is sufficient. However, multiple doses can also be administered at intervals of 6-24 hr.

Where desired, treatment can be initiated either before a triggering event that promotes the episode, or just after the subject experiences an aura that typically precedes the onset of an observable seizure in the subject. The agent is optionally administered at least about 50.5, 1, 2, 3, 4, 5, 6, 8, 12, 24 or 48 hours before of an epileptic seizure.

In other situations, treatment can be administered at a desired timepoint after initiation of an epileptic seizure. The agent is for example administered at least about 0.1, 0.5, 1, 2, 3, 4, 5, 6, 8, 12, 24 or 48 hours after the initiation of an epileptic seizure. The epileptic seizure can be shortlived, e.g., lasting under a second, or a few seconds, or about one or a few minutes, or about half an hour.

The methods of the invention can be combined with other treatments for epilepsy. Such conventional treatments include behavioral therapy, lifestyle changes and/or pharmaceutical therapy. Known anti-epileptic drugs include "traditional" medications such as phenobarbital, primidone, phenyloin, carbamazepine, and valproate; as well as newer antiepileptic drugs that induce voltage-dependent ion channel blockade, enhancement of inhibitory neurotransmission, and/or reduction of excitatory neurotransmission. Examples include glutamate antagonism at N-methyl-D-aspartate (NMDA) receptors (e.g., felbamate) and α-amino-3-hydroxy-5-methyl-4-isoxazole propionic acid (AMPA) receptors (e.g., felbamate, topiramate) and inhibition of γ-aminobutyric acid (GABA) reuptake in neurons and astrocytes (e.g., tiagabine).

Suitable antiepileptics include sodium channel blockers, GABA receptor agonists, GABA reuptake inhibitors, GABA transaminase inhibitors, glutamate blockers, as well as antiepileptic agents with other mechanisms of action. Anti-epileptic drugs include aldehydes, aromatic allylic alcohols, barbiturates, benzodiazepines, bromides, carbamates, carboxamides, fatty acids, fructose derivatives, gaba analogs, hydantoins, oxazolidinediones, propionates, pyrimidinediones, pyrrolidines, succinimides, sulfonamides, triazines, ureas, valproylamides (amide derivatives of valproate). Specific examples of commonly used antiepileptic agents include acetazolamide, acetazolomide modified release, carbamazepine, carbamazepine modified release, clobazam, clonazepam, ethosuximide, gabapentin, lamotrigine, levetiracetam, oxcarbazepine, phenobarbital (phenobarbitone), phenyloin, pregabalin, primidone, rufinamide, sodium valproate, sodium valproate modified release, tiagabine, topiramate, valproic acid, vigabatrin or zonisamide. Any combination of such drugs or their derivatives can be used.

VI. Pharmaceutical Compositions, Dosages and Routes of Administration

The peptides and peptidomimetics of the invention can be administered in the form of a pharmaceutical composition. Pharmaceutical compositions are manufactured under GMP conditions. Pharmaceutical compositions can be provided in unit dosage form (i.e., the dosage for a single administration) containing any of the dosages indicated below. Pharmaceutical compositions can be manufactured by means of conventional mixing, dissolving, granulating, dragee-making, levigating, emulsifying, encapsulating, entrapping or lyophilizing processes. In particularly, lypholyized peptides or peptidomimetics of the invention can be used in the formulations and compositions described below.

Pharmaceutical compositions can be formulated in conventional manner using one or more physiologically acceptable carriers, diluents, excipients or auxiliaries that facilitate processing of peptides or peptidomimetics into preparations which can be used pharmaceutically. Proper formulation is dependent on the route of administration chosen.

Administration can be parenteral, intravenous, oral, subcutaneous, intraarterial, intracranial, intrathecal, intraperitoneal, topical, intranasal or intramuscular. Intravenous administration of the drug in a phosphate buffered saline solution is preferred.

Figure 14:
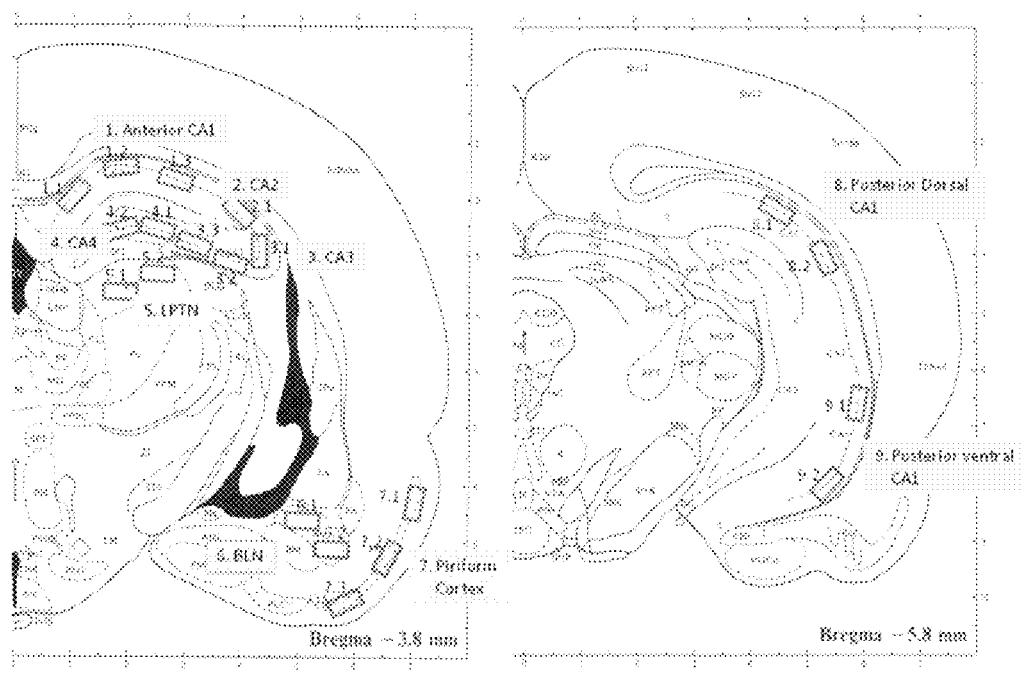
FIG. 14. Map of the brain and various areas within the brain.

The invention is intended to treat neurodegeneration in any part of the brain, Various areas of the brain are shown in FIG. 14.

Pharmaceutical compositions for parenteral administration are preferably sterile and substantially isotonic. For injection, peptides or peptidomimetics can be formulated in aqueous solutions, preferably in physiologically compatible buffers such as Hanks's solution, Ringer's solution, or physiological saline or acetate buffer (to reduce discomfort at the site of injection). The solution can contain formulatory agents such as suspending, stabilizing and/or dispersing agents.

Alternatively the peptides or peptidomimetics can be in powder form for constitution with a suitable vehicle, e.g., sterile pyrogen-free water, before use.

For transmucosal administration, penetrants appropriate to the barrier to be permeated are used in the formulation. This route of administration can be used to deliver the compounds to the nasal cavity or for sublingual administration.

For oral administration, the compounds can be formulated by combining the peptides or peptidomimetics with pharmaceutically acceptable carriers as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate. If desired, solid dosage forms can be sugar-coated or enteric-coated using standard techniques. For oral liquid preparations such as, for example, suspensions, elixirs and solutions, suitable carriers, excipients or diluents include water, glycols, oils, alcohols. Additionally, flavoring agents, preservatives, coloring agents and the like can be added.

In addition to the formulations described previously, the compounds can also be formulated as a depot preparation.

Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions can be used to deliver peptides and petidomimetics. Certain organic solvents such as dimethylsulfoxide also can be employed, although usually at the cost of greater toxicity. Additionally, the compounds can be delivered using a sustained-release system, such as semipermeable matrices of solid polymers containing the therapeutic agent.

Sustained-release capsules can, depending on their chemical nature, release the peptides or peptidomimetics for a few weeks up to over 100 days. Depending on the chemical nature and the biological stability of the therapeutic reagent, additional strategies for protein stabilization can be employed.

As the peptides or peptidomimetics of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The agents of the invention are used in an amount effective to achieve the intended purpose. A therapeutically effective amount means an amount of agent sufficient to eliminate, reduce or inhibit worsening of at least one sign and/or symptoms of epilepsy or a subtype thereof in patient presently experiencing symptoms of epilepsy. For example, an amount is considered therapeutically effective if it significantly reduces at least one sign or symptom of epilepsy in a population of treated patients (human or animal) compared with a control population of untreated patients. The amount is also considered therapeutically effective if an individual treated patient achieves an outcome more favorable than the mean outcome in a control population of comparable patients not treated by methods of the invention. A prophylactically effective amount of an agent means an amount of agent sufficient to delay, inhibit or prevent development of at least one sign or symptom of epilepsy or a subtype thereof in a patient not currently experiencing symptoms but who is considered at heightened risk relative to the general population of developing such symptoms. For example, an amount is considered to be prophylactically effective if a population of patients at risk of developing symptoms of epilepsy treated with the agent develops reduced signs or symptoms relative to a control population not treated with the agent. Reference to an effective amount means either a therapeutically or prophylactically effective amount. Reference to an effective regime means a combination of an effective amount and dosing frequency required to achieve the intended purpose as described above.

Preferred dosage ranges include about 0.01 to 100 µmol agent per kg patient body weight, optionally 0.1 to 10 µmol agent per kg patient body weight, e.g., 0.5 to 2 µmol agent per kg patient body weight, or about 1 µmol agent per kg patient body weight. In some methods, 0.1-10 µmol agent per kg patient body weight are administered. In some methods, 0.5-5 µmol agent per kg patient body weight is administered within 6 hours, more preferably about 1 µmol agent per kg patient body weight at about 3-6 hours after an epileptic seizure. In other instances, the dosages range is from 0.05 to 0.5 µmol agent per kg patient body weight. Dosage per kg body weight can be converted from rats to humans by dividing by 6.2 to compensate for different surface area to mass ratios. Similarly, dosage per kg body weight can be converted from mice to humans by dividing by 12.3. Dosages can be converted from units of moles to grams by multiplying by the molar weight of a peptide (here, 2519 for Tat-NR2B9c). Dosages can be converted from units of moles to grams by multiplying by the molar weight of a peptide. Suitable dosages of peptides or peptidomimetics of the invention for use in humans can include about 0.01 to 100 mg/kg patient body weight, or more preferably about 0.1 to 10 mg/kg patient body weight or about 0.5 to 5 mg/kg, or about 1-4 mg/kg, e.g., about 2.6 mg/kg. In absolute weight for a 75 kg patient, these dosages translate to 0.75-7500 mg, 7.5 to 750 mgs, 37.5-3750 mgs, or about 75-300 mgs, e.g., about 200 mgs. Rounded to encompass variations in e.g., patient weight, the dosage is usually within 0.05 to 500 mg, preferably 0.1 to 100 mg, 0.5 to 50 mg, or 1-20 mg.

Alternatively, agents such as Tat-NR2B9c intended for use in the present methods have previously been reported to be useful for treating stroke and have undergone phase I clinical trials for this indication without serious adverse events. The dosages and regimes used for treating stroke can also be used for epilepsy, particularly short intermittent seizures of epilepsy.

The amount of agent administered depends on the subject being treated, on the subject's weight, the severity of the affliction, the manner of administration and the judgment of the prescribing physician. The therapy can be repeated intermittently while symptoms detectable or even when they are not detectable. The therapy can be provided alone or in combination with other drugs.

Therapeutically effective dose of the agents can provide therapeutic benefit without causing substantial toxicity. Toxicity of the peptides or peptidomimetics can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Peptides or peptidomimetics exhibiting high therapeutic indices are preferred (see, e.g., Fingl et al., 1975, In: *The Pharmacological Basis of Therapeutics*, Ch. 1, p. 1).

VII. Screening Methods

The invention further provides methods of screening peptides, peptidomimetics and other compounds for activity useful in treating epilepsy. Compounds are administered to an animal model of epilepsy. Various animal models are discussed below.

Compounds suitable for screening in the methods include peptides, peptidomimetics and small molecules (i.e., less than 500 Da) known to inhibit interactions of ligands with the PDZ domains of PSD-95, including NDMAR 2B. Other peptides, peptidomimetics and small molecules known to inhibit interactions between other pairs of NDMAR and PDZ domain proteins shown in Table 1 can also be screened.

Compounds to be screened can be both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds.

Compounds can be prepared from diversity libraries, such as random or combinatorial peptide or non-peptide libraries. Libraries include chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994, *Proc. Natl. Acad. Sci. USA* 91:1614-1618; Salmon et al., 1993, *Proc. Natl. Acad. Sci. USA* 90:11708-11712; WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science*, 249:404-406; Christian, R. B., et al., 1992, *J. Mol. Biol.* 227:711-718); Lenstra, 1992, *J. Immunol. Meth.* 152: 149-157; Kay et al., 1993, *Gene* 128:59-65; WO 94/18318 dated Aug. 18, 1994. In vitro translation-based libraries include those described in WO 91/05058; and Mattheakis et al., 1994, *Proc. Natl. Acad. Sci. USA* 91:9022-9026. By way of examples of nonpeptide libraries, a benzodiazepine library (see e.g., Bunin et al., 1994, *Proc. Natl. Acad. Sci. USA* 91:4708-4712) can be adapted for use. Peptoid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

Animal Models of Epilepsy:

A wide number of animal models of different epileptic conditions are well characterized. See, e.g., Models of Seizures and Epilepsy, edited by: Asla Pitkänen, Philip A. Schwartzkroin and Solomon L. Moshe, ISBN: 978-0-12-088554-1; Elsevier Inc., Copyright © 2006, incorporated by reference in its entirety. The animals can vary from drosophila to primates, in which epilepsy is brought about in a variety of ways including by administration of chemicals or genetic screening for specimens that spontaneously develop seizures and/or epilepsy Examples of animal models include hyperthermia-induced seizures in rats that mimics febrile seizures, mouse mutants such as totterer, stargazer, lethargic, and slow wave epilepsy (SWE) mice that share characteristics similar to human absence epilepsies such as brief behavioral arrest (i.e., staring or gazing);

Well-characterized animal models have also beed described for complex partial seizures observed in patients with temporal lobe epilepsy (TLE). The kainic acide and pilocarpine (PILO) seizure models are probably the most commonly studied chemical-inductive animal models for TLE. Kindling, a phenomenon whereby repetitive, focal application of initially subconvulsive electrical stimulation ultimately results in intense partial and generalized convulsive seizures, continues to be an informative model for TLE.

In addition, several genetically epilepsy-prone species have been described as animal models for studying photosensitive and audiogenic reflex epilepsies. These include the baboon Papio papio, the Fayoumi epileptic (FEpi) strain of chickens, the genetically epilepsy prone rat (GEPR) and DBA/2 mice.

A variety of methods are available for inducing generalized tonic clonic or absence seizures in animals, as are some genetic animal models that are either highly seizure-prone or have spontaneous seizures. The following are a few traditional methods of eliciting such seizure types.

Convulsive seizures, characterized by tonic hindlimb extension/flexion followed by clonic activity, are reliably induced by maximal electroshock which continues to be a popular method for the rapid screening of new anticonvulsant drugs.

Pentylenetetrazol (PTZ) is probably the most widely used systemically administered convulsant. Repeated injections of PTZ can be given to produce a type of chemical kindling that resembles electrical kindling. At high doses, PTZ (usually administered subcutaneously or intravenously) reliably produces tonic clonic convulsions in rats or mice and is a rapid and efficient measure of both seizure susceptibility and screening of new drugs. Given systemically at low doses, PTZ can also be used to elicit absence-like seizures.

Fluorothyl, a hexafluorinated ether, is a chemical inhalant used to induce a reproducible convulsive seizure pattern in rodents. In this method, rats or mice are placed in an airtight chamber into which centrally administered fluorothyl diffuses; after 10-20 min fluorothyl initially causes myoclonic jerks followed by severe clonic-tonic convulsions. Finally, other experimental animal models for generalized absence seizures include thalamic stimulation, systemic penicillin administration in cat, g-hydroxybutyrate treatment (GHB), and intracerebroventricular opiates, as well as the number of genetic models in rats (GAERS, WAG/Rij, SER) and mice (stargazer, tottering, lethargic, slow-wave epilepsy mice, mocha, and ducky) already described.

Animal models such as those described above, both in vivo and in vitro, have been valuable in understanding basic mechanisms of partial or generalized seizure-related phenomena and are standard techniques for evaluating new therapeutics. Sarkisian, Epilepsy & Behavior 2, 201-216 (2001), incorporated by reference in its entirety.

EXAMPLES

Example 1

Pilocarpine Rat Model of Epilepsy

A. Cannulation of the Femoral Vein

Animals were anaesthetized for approximately 40 minutes under a continuous supply of 3% isoflorane and positioned in dorsal recumbence on a heating pad during surgery. The surgical sites were cleaned and shaved with Betadine soap. A 3 cm ventral skin incision was made from the lower right quadrant of the abdomen and along the right thigh, next to a discernible crease marking the position of the femoral vein, femoral artery, and sciatic nerve. Minimal dissection of the adductor muscles was performed to visualize the vascular bundle, and the femoral vein, femoral artery and sciatic nerve was carefully separated. A small nick was made in the femoral vein, and a P10 polyethylene cannula, prefilled with physiological saline containing heparin (1 mL heparin/1 L PBS), was inserted 4 to 5 cm. Multiple 4.0 silk sutures were ligated around the femoral vein, femoral artery, sciatic nerve to secure the cannula. The animal was placed in a ventral recumbence, and a 0.5 cm dorsal midline skin incision was made between the scapulae. A metal tube 15 cm in length with an unblunted end was inserted through the dorsal midline incision and subcutaneously tunneled to the ventral thigh incision. The free end of the cannula was fed through the metal tube and extruded from the dorsal midline incision. The metal tube was removed and the ventral skin incision was closed. The cannula was secured by being woven through a plastic surgical button, flushed with physiological saline containing heparin, and sealed with a 23-gauge pin. The dorsal incision was closed, and the plastic surgical button was sown with 4.0 silk suture between the scapulae, a strategic region that remained out of reach for the animal during the 5 day recovery period that followed.

B. Induction of Epileptic Seizures

Male Wistar rats between 350 to 400 grams were pretreated with lithium chloride (ip; 3 mEq/kg) 17 to 24 hours before systemic injection of the chemoconvulsant pilocarpine. Pilocarpine (ip; 10 mg/kg) was administered every 30 minutes until onset of status epilepticus (SE), which was defined as a loss of consciousness and continuous overt seizure activity. In the low-dose pilocarpine (LDP) method, LEH or Wistar rats were administered an initial injection of pilocarpine (30 mg/kg, i.p.). If SE did not develop within 60 minutes, a second pilocarpine injection (15 mg/kg) was administered. In the second procedure, the repeated low-dose pilocarpine (RLDP) method, pilocarpine (10 mg/kg, i.p.) was administered to LEH or Wistar rats every 30 min as described by Glien et al, (Epilepsy Res. 2001 August; 46 (2):111-9) until the rat experienced a generalized, class 4/5 seizure. Rats generally developed SE shortly thereafter. Animals that did not develop SE within 30 min of the first class 4/5 seizure, received additional pilocarpine injections at 30-min intervals up to a maximum of 6 injections. SE was terminated at 1, 3 and 5 hours following onset of SE with diazepam (ip; 4 mg/kg). Overt seizure activity that occurred during SE was recorded into stages using a modified Racine scale (Racine, 1972) as follows: 1) mouth movements, 2) mouth movements and head nodding, 3) forelimb clonis, 4) forelimb clonis and rearing, 5) forelimb clonis, rearing and one fall, 6) forelimb clonis, rearing and multiple falls, and 7) running and jumping. Our modified Racine scale further separated the original class five into three stages to account for seizure activity involving multiple falls (6) and running and jumping (7).

C. Assessment of Neurodegeneration Following Epileptic Seizures

Animals were anaesthetized with ketamine and Romptum, and transcardially perfused with paraformaldehyde (PFA; 4% in 0.1 M phosphate buffer, pH 7.4) 2 weeks after SE induction. Brains were removed, post-fixed overnight in PFA, and then equilibrated in 30% sucrose in PBS. Brains were then frozen at −35° C. in methylbutane and stored until further use at −70° C. in scintillation vials containing frozen 30% sucrose in PBS to prevent freezer drying. The brains were coronally sectioned at 40 μm using a freezing microtome and stored at −20° C. in 24-well plates containing antifreeze solution (15% glucose, 30% ethylene glycol, 50 mMol phosphate buffer; pH 7.4).

For each animal, neuronal cells were quantified by immunohistochemical staining with NeuN, a neuronal cell specific antibody. Free floating sections were rinsed (3 minutes×2) in 0.1 M PBS before being incubated overnight in primary neuron-specific antibody NeuN (1:1000), 0.3% Triton X-100, and 2% goat serum at 4° C. shaking slowly. Sections were washed (3 minutes×3) in 0.1 M PBS and incubated with anti-mouse secondary antibody conjugated to Cy3 (1:200) and 0.3% Triton X-100 for 2 hours at room temperature. Brain sections were rinsed (3 minutes×3) and mounted on gelatin-coated slides. Sections were allowed to air dry before being placed in 100% alcohol for 1 minute, cleared in xylene for 3 minutes, and coverslipped with Permount.

NeuN-immunoreactive cells were counted using the optical dissector method (40× objective) in 3 sections spaced 240 μm apart along the rostrocaudal axis of the dorsal hippocampus (bregma-2.8 to -3.8 mm). Sections selected were comparable between animals. Within the CA1 region, 3 counting boxes (counting frame=60×120 μm, dissector height=40 μm) per section were distributed in a systematically random manner. The Z-stack images of the counting frames taken at overlapping 0.7 μm intervals were saved and exported as 2564×2051 JPEG gallery images in the Zeiss LSM Image Browser software. The JPEG gallery images were imported and quantified using ADOBE Photoshop 7.0. A total of 9 counting boxes per animal were quantified for the anterior CA1 region. Results are presented as an average of the total number of cells quantified per counting frame.

Example 2

Effects of Epileptic Seizures on the Brain in a Rat Model

Status epilepticus was induced in male Wistar rats as described in Example 1. The effects of epileptic seizures on the brain of these rats were characterized as described below.

A. Characterization of SE-Induced Neuropathology

Neurodegeneration was assessed using stereological analysis with the optical dissector method and staining for NeuN to quantify neurons. Three coronal sections per animal were analyzed, and 60-100 neurons were counted per brain section in a naïve animal. Cell counts were performed at, 3 hrs, 6 hrs, 12 hrs, 24 hrs, 3 days, 7 days, 14 days, and 3 months following the termination of SE. All animals developed SRSs between 3 and 8 weeks. At least 4 animals were included in all groups. To date, the following brain regions have been analyzed: pyramidal layer of the hippocampal subfields anterior CA1, CA2, CA3, CA4, posterior dorsal CA1 and posterior ventral CA1 (D&V), basolateral amygdaloid nuclei (BLN), lateral posterior thalamic nuclei (LPTN) and piriform cortex.

Maximum cell loss occurred within 3 days for all brain regions, with the exception of the posterior CA1 (see FIGS. 1 and 2). The occurrence of spontaneous recurrent seizures did not contribute to further cell loss in these brain regions, indicating neurodegeneration specifically occurs as a consequence of sustained SE. The CA2 and CA3 subfields of the hippocampus appeared to be somewhat less susceptible to cell loss (FIGS. 2 and 3). The anterior and posterior CA1 subfields were the most severely affected regions of the hippocampus (>70% cell loss). In addition, the LPTN, BLN and piriform cortex are also severely affected (<80% cell loss).

Staining with the neuron-specific antibody NeuN detects neurodegeneration by the absence of NeuN-positive cells; that is, at the end of the neurodegeneration process. In contrast, fluoro-jade B (FJB) staining detects dying neurons prior to endpoint pathology. Double staining with NeuN and FJB following SE allowed early detection of neurodegeneration. For example, in the basolateral amygdaloid nuclei FJB staining appeared in 8±13% of neurons as early as 3 hrs, in 30±6% of neurons at 6 hrs, and in 54±7% of neurons at 24 hrs following SE. Thus a rapid initiation of processes contributing to neurodegeneration following SE was detected, with cell loss detected as early as 6 hrs post-SE.

Example 3

TAT-NR2B9C Rescues Neuron Loss in Dorsal CA1 Region Following Epileptic Seizures Status epilepticus was induced in male Wistar rats as described in Example 1. Tat-NR2B9c (3 nmol/gm in physiological saline) was administered via the femoral vein 3 hours following termination of SE at a constant rate of 60 µm per minute. The rats were allowed to recover for 14 days after SE and then analyzed.

Figure 6:
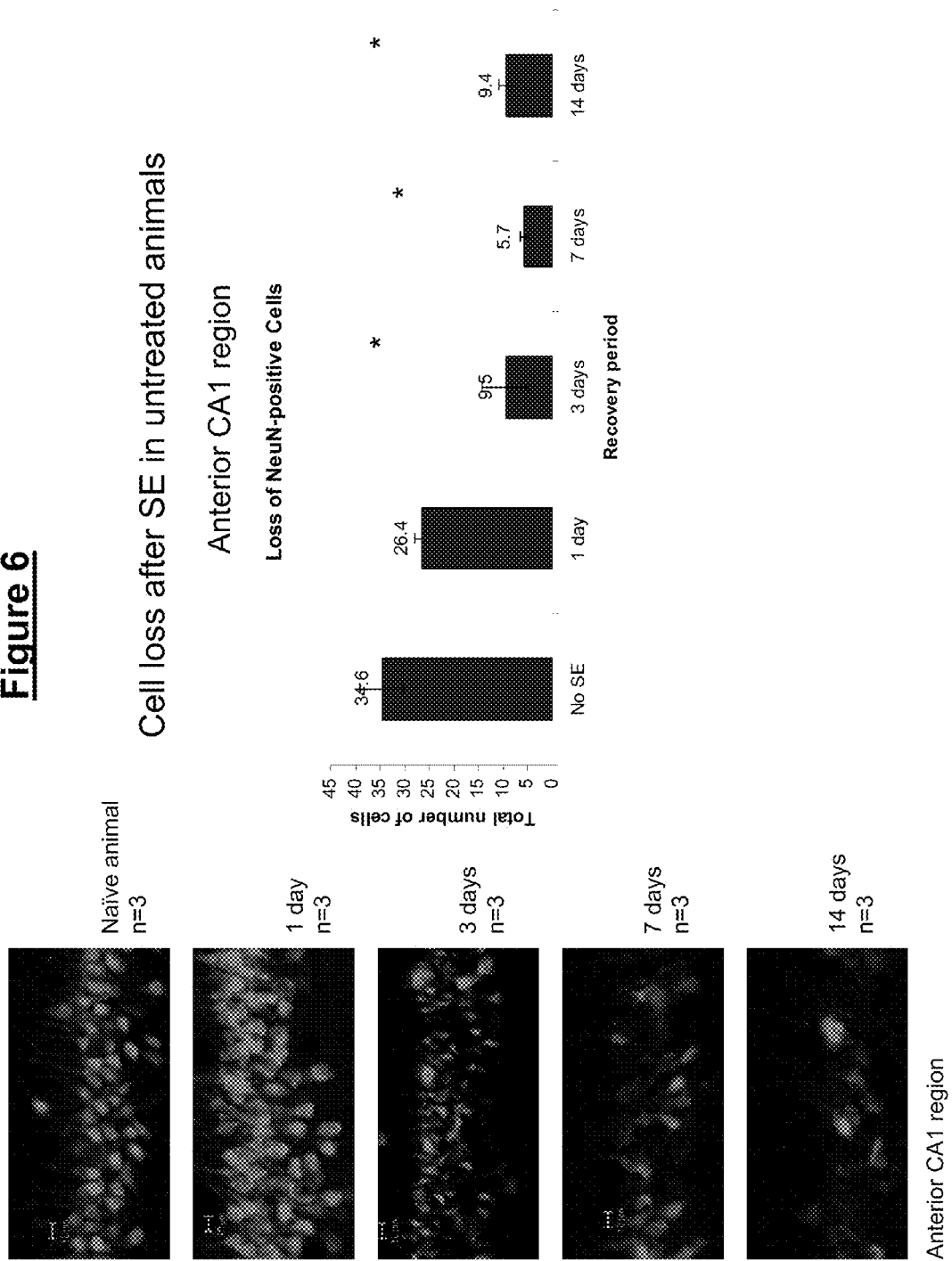
FIG. 6. Time course of neuronal (NeuN-positive) cell loss over 1, 3, 7 and 14 days after induction of a state of continuous epileptic seizure for 60 minutes in animals that were not treated with Tat-NR2B9c. 400× magnification of brain sections are shown on the left. The column graph depicts the total number of NeuN-positive cells per field±standard deviation at various timepoints.

Neurodegeneration was assessed in terms of loss of NeuN-positive cells as described in Examples 1 and 2. The typical time course of neuronal cell loss after induction of epileptic seizures is shown in FIG. 6. Cell loss is maximal at about 7 days post-SE, a depletion that remains by day 14.

Figure 8:
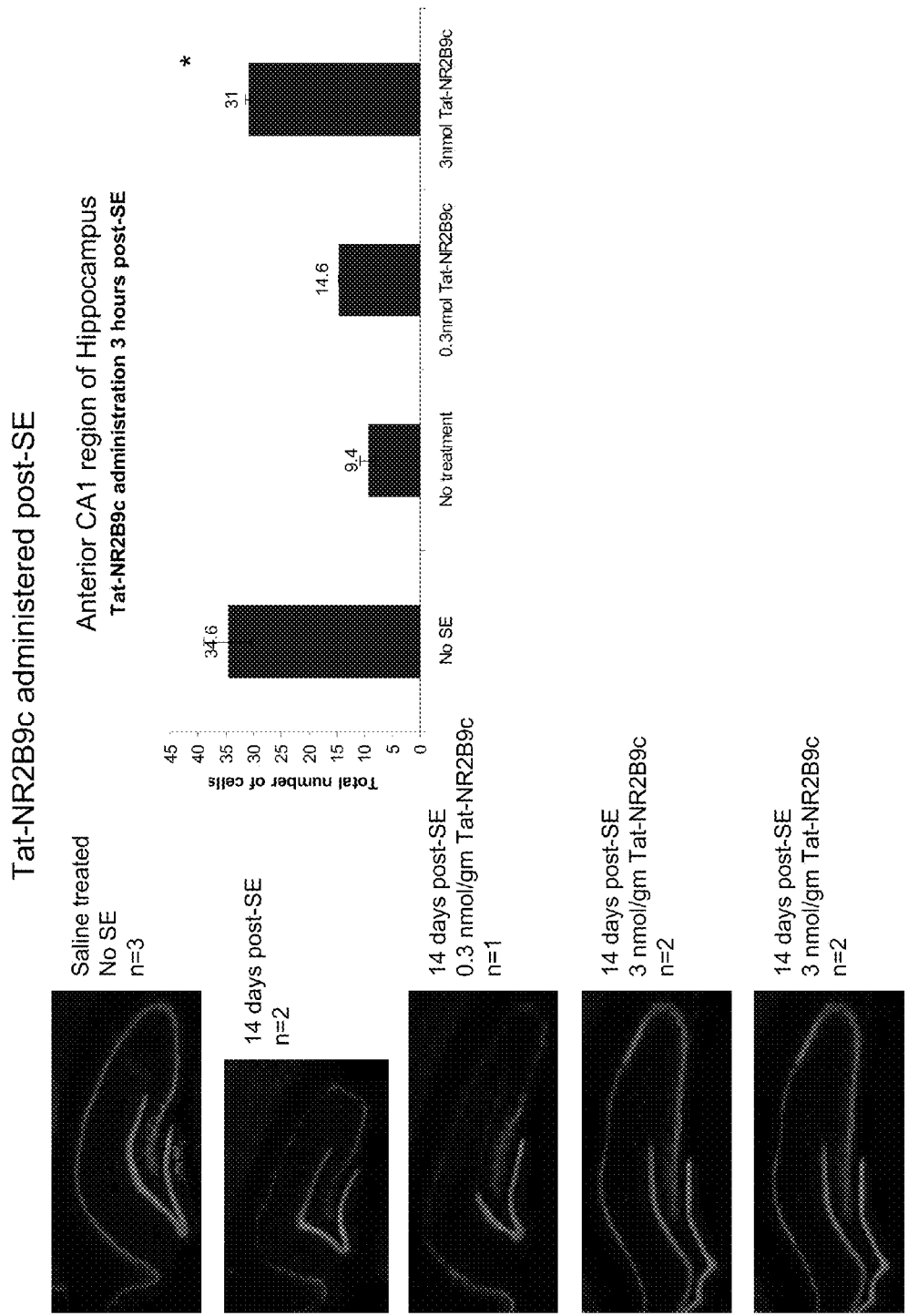
FIG. 8. Time course of neuronal (NeuN-positive) cell loss after induction of epileptic seizures in rats that were then treated with Tat-NR2B9c three hours after epileptic seizure. A view of immuno-stained brain sections at low magnification are shown on the left. The column graph depicts the total number of NeuN-positive cells per field±standard deviation after 14 days of recovery at different concentrations of Tat-NR2B9c.
Figure 9:
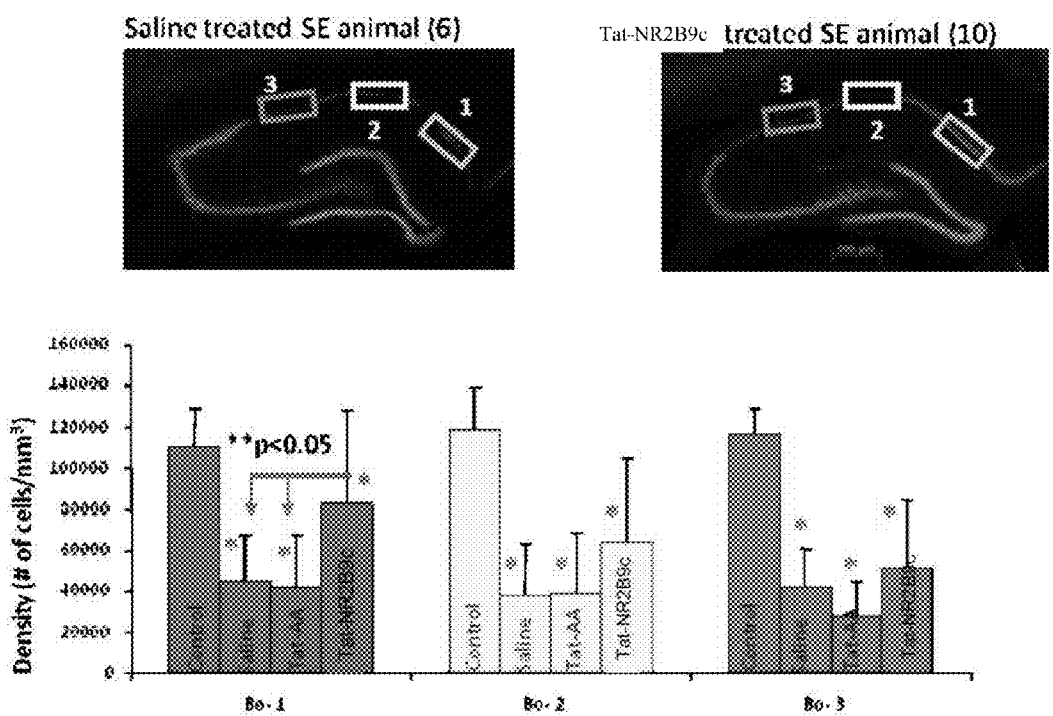
FIG. 9. Tat-NR2B9c neuroprotection near the subicular border of the CA1 region. Tat-NR2B9c increased the number of surviving neuronal cells compared to saline-treated animals. while Tat-NR2BAA did not.
Figure 10:
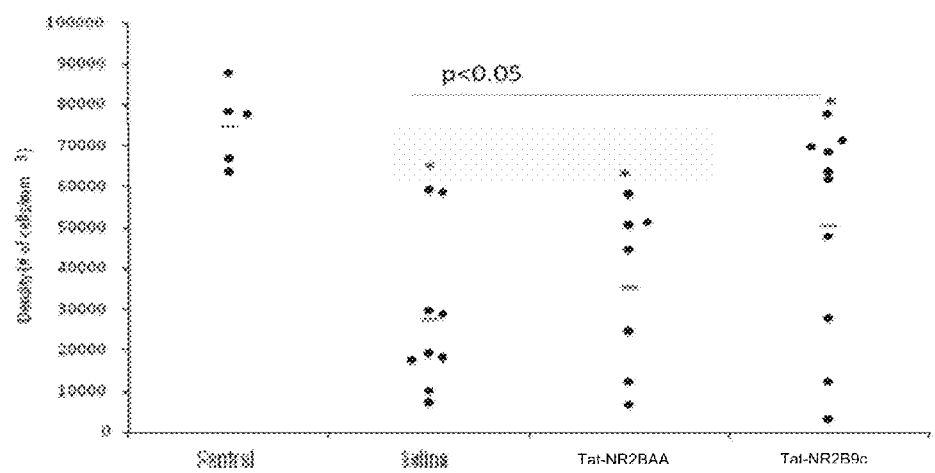
FIG. 10. Tat-NR2B9c confers neuroprotection in the CA4 region while Tat-NR2BAA does not.

As shown in FIG. 8, Tat-NR2B9c rescued neuron loss in a dose-dependent manner when administered to rats at about 3 hours after induction of epileptic seizures. In contrast, a control peptide Tat-NR2BAA did not decrease neurodegeneration (FIG. 4A).

Figure 7:
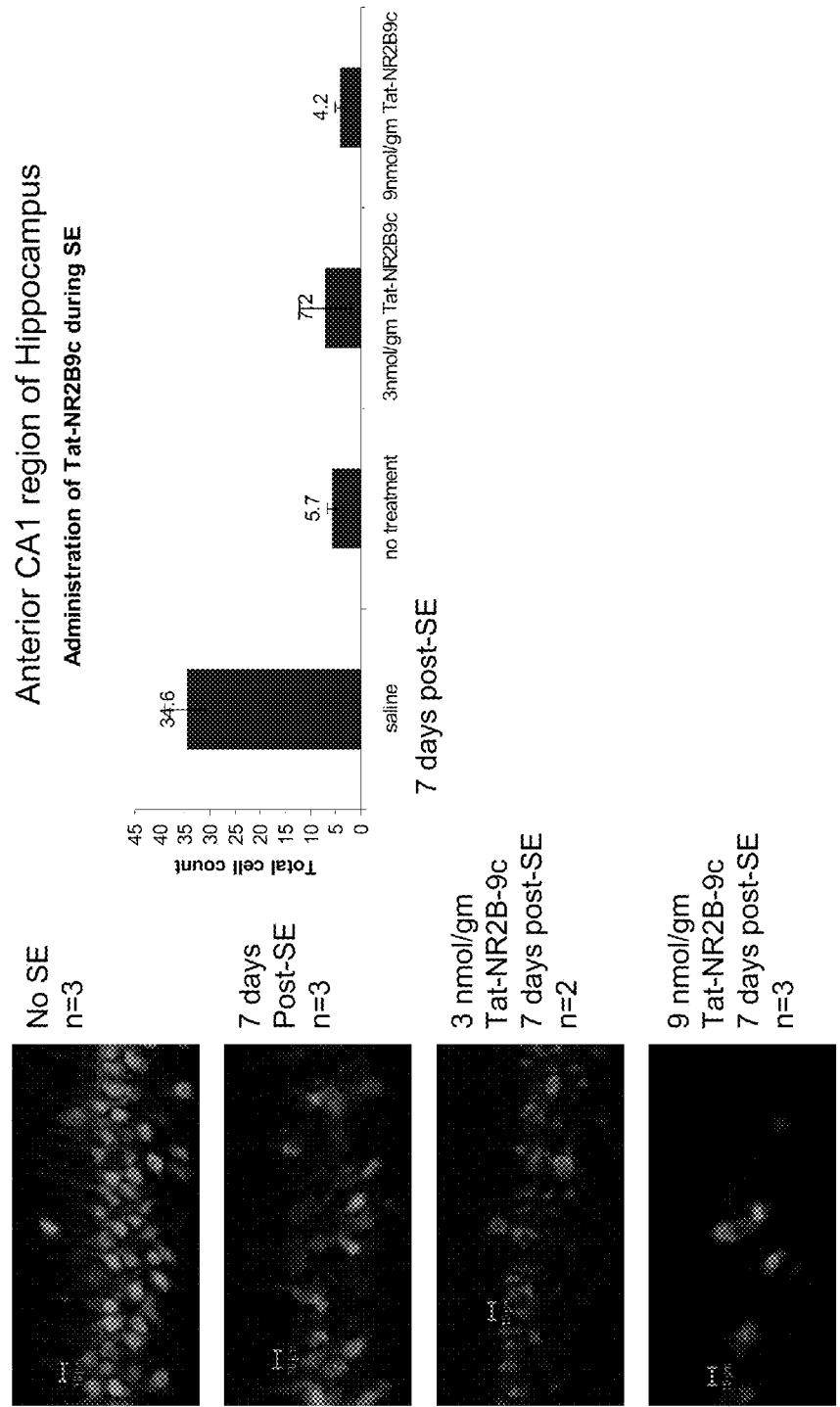
FIG. 7. Time course of neuronal (NeuN-positive) cell loss at 7 days after induction of a state of continuous epileptic seizure for 60 minutes in animals that were treated with Tat-NR2B9c during status epilepticus. 400× magnification of brain sections are shown on the left. The column graph depicts the total number of NeuN-positive cells per field±standard deviation at different concentrations of Tat-NR2B9c.

In surprising contrast, Tat-NR2B9c administered to rats during a state of continuous epileptic seizure did not decrease neuron loss (FIG. 7). This result is especially surprising in light of previous studies showing that Tat-NR2B9c is highly neuroprotective in animal models of stroke when applied before or 1 hour after a stroke (Aarts et al, 2002), and effective to 3 hours following the neurological insult and beyond.

Figure 4B:
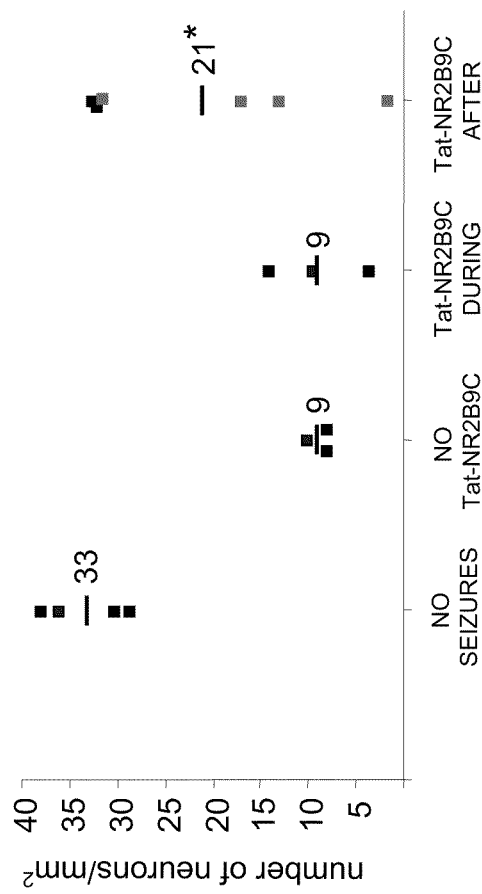
Figure 5:
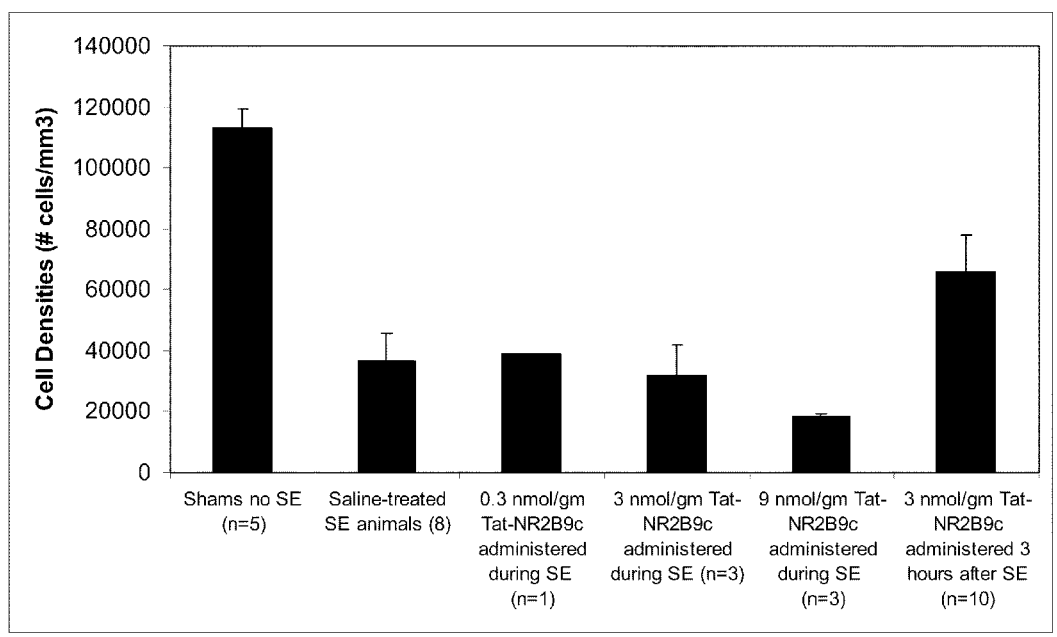
FIG. 5. Tat-NR2B9c conferred dose-dependent neuroprotection when administered 3 hours after, but not during, epileptic seizure. Columns 1 and 2: shams (rats in which epileptic seizures were not induced) and seizure-induced rats administered saline, respectively. Columns 3, 4, 5: Tat-NR2B9c administered 10 minutes following initiation of SE, at a dosage of 0.3 nmol/gm, 3 nmol/gm and 9 nmol/gm, respectively. Column 6: 3 nmol/gm Tat-NR2B9c administered 3 hours following termination of SE.

Tat-NR2B9c was especially protective in the anterior CA1 region, while the negative control peptide Tat-NR2BAA, that cannot act as a PSD-95 antagonist, was not (FIG. 4A). A comparison of the differential effects of Tat-NR2B9c depending on timing of administration relative to epileptic seizures is presented in FIGS. 5 and 4B. Neuron loss in rats administered Tat-NR2B9c during status epilepticus was comparable to neuron loss in untreated rats even at high doses of Tat-NR2B9c (9 nmol/gm) (FIGS. 4B, 5 and 7). In striking contrast, lower doses of Tat-NR2B9c (0.3 nmol/gm and 3 nmol/gm) conferred neuroprotection (FIGS. 4B, 5 and 7) when given after the termination of status epilepticus.

Example 4

Histochemical Visualization of Neuroprotection Following Epileptic Seizures by TAT-NR2B9C Seizures were induced in male Wistar rats and Tat-NR2B9c was administered 3 hours following the insult, as described in Examples 1 and 2. Brains were fixed, sectioned, and immunostained with NeuN as described above. Coronal sections of the dorsal hippocampus were visualized under a microscope at 2.5×, and representative pictures are shown below. FIG. 8, left panel shows increased NeuN-immunostaining as a result of Tat-NR2B9c administration, with the best results (closest to the no-SE control) obtained with the higher amount of Tat-NR2B9c.

When sections of the dorsal CA1 region of the hippocampus were viewed under 40× magnification, the number of NeuN stained cells was greatly diminished in the pilocarpine treated rats as compared to the saline treated rats. This effect was reversed by the administration of Tat-NR2B9c (FIG. 8, left panel).

Example 5

TAT-NR2B9C Dramatically Reduces the Size of Lateral Ventricles Following SE

Following pilocarpine and Tat-NR2B9c administration, and fixing of brain sections, as described above, every 6$^{th}$ section was used for Nissl staining with cresyl violet. Sections were mounted and allowed to air dry on gelatin coated slides. The sections were rehydrated in an alcohol series at 100%, 95%, 70%, and 50% each for 5 minutes. The sections are then placed in water for 1 minute, followed by the Cresyl Violet Stain for 20 to 30 minutes. Sections are rinsed (30 seconds×2) in water, and dehydrated in an alcohol series at 50% for 5 minutes (or less), 70% for 5 minutes (or less), 95% for 5 minutes (or less), 100% for 5 minutes (or less), and 100% for 5 minutes (or less). Differentiation occurs maximally at the 50% and 70% alcohol gradients. Sections were cleared in xylene for 5 minutes and coverslipped with Permount, and viewed, e.g., under 40× magnification.

While the rats who underwent seizures had very large lateral ventricles, administration of Tat-NR2B9c reduced them to the size found in rats who had not been given pilocarpine.

Figure 11:
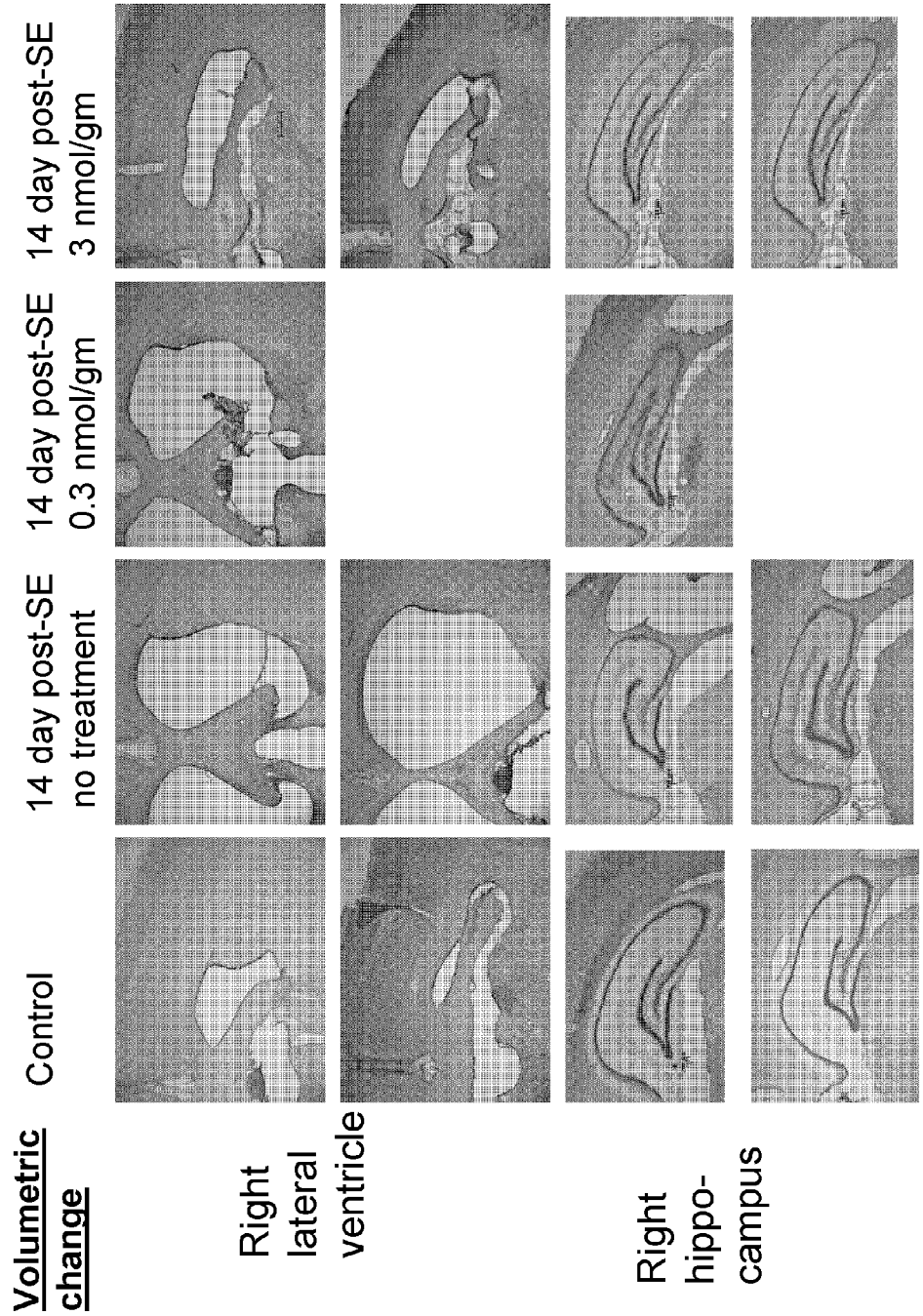
FIG. 11. Volumetric changes in the hippocampus and lateral ventricles 14 days post-SE in rats left untreated (control) or treated at 3 hours post-SE with Tat-NR2B9c (0.3 nmol/gm and 3 nmol/gm), with a side-by-side comparison of Nissl stained sections in (A) the lateral ventricles, and (B) the hippocampus.

FIG. 11 shows a dramatic reduction of lateral ventricle size in animals treated with Tat-NR2B9c at 3 hours post-SE. At comparable Niss1 stained sections, animals treated with Tat-NR2B9c at 3 hours post-SE had noticeably smaller lateral ventricles than compared to non-treated animals.

Example 6

Tat-NR2B9c Ameliorates Cognitive Impairment Caused by Epileptic Seizures

We investigated possible behavioral effects of 60 min SE induced with the RLDP procedure. Visual-spatial memory was investigated with the Morris water maze (MWM) at 8 weeks post-SE to detect chronic cognitive impairment. The MWM is of particular usefulness with studies involving therapeutic agents, since the severity of neurodegeneration in the anterior CA1 region is strongly correlated with performance (escape latency) (Clasussen et al, 2005). Four groups of animals were compared in the present analysis: 1) controls that received saline instead of pilocarpine and did not enter SE, 2) no SE group that received up to 6 repeated low doses of pilocarpine but did not enter SE, 3) SE group that entered SE induced by the RLDP procedure, and 4) Tat-NR2B9c group that entered SE induced by the RLDP procedure and was administered the Tat-NR2B9c drug at 3 hours post-SE via femoral vein cannulation (results obtained with Tat-NR2B9c will be discussed in section 4)). All groups contained at least 6 animals.

Figure 12:
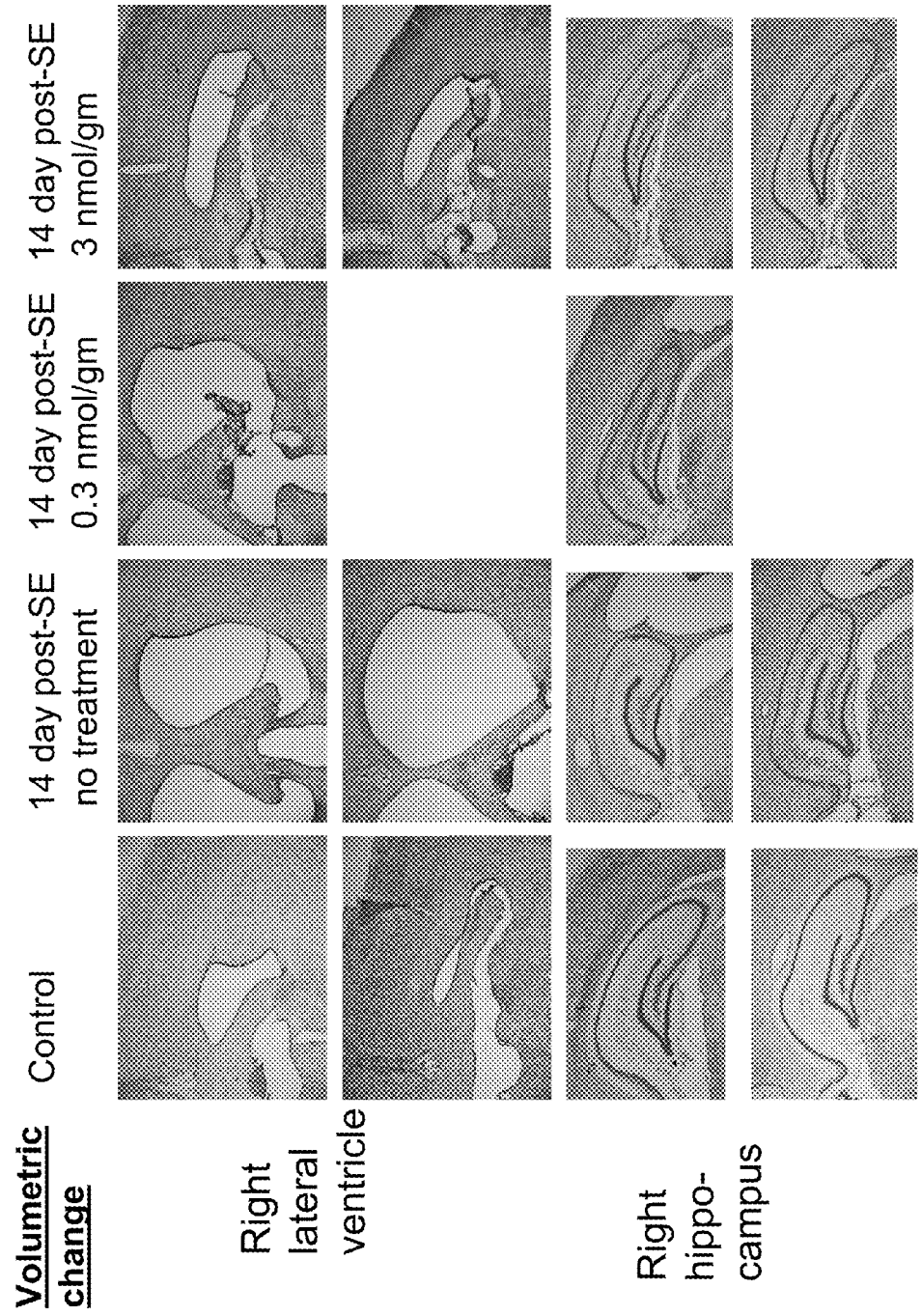
FIG. 12. Tat-NR2B9c reduces the cognitive impairment caused by status epilepticus in rats. At 8 weeks post-SE, animals were placed on the elevated plus maze for 5 minutes and videotaped.

Various cognitive functions of epileptic mice treated or untreated with Tat-NR2B9c were assessed as follows:
i) Elevated Plus Maze:
The elevated plus maze is used to investigate exploratory behaviour. At 8 weeks post-SE, animals were placed on the elevated plus maze for 5 minutes and videotaped. SE animals spent less time (50%) in the closed arm, as compared to controls (86%), and had a greater number of entries into the open arm and fewer entries into the closed arm (FIG. 12A-D). Furthermore, SE animals had reduced frequency of lookouts into the open arm and rearing episodes when compared to controls (FIGS. 12 E & F). Tat-NR2B9c-treated animals, when compared to untreated animals, decreased these effects of SE on exploratory behavior.
ii) Morris Water Maze:
We found that the SE rats exhibited clear improvement in performance over repeated trials and days (FIG. 13). In our study animals were trained on the MWM task for 14 consecutive days, with 6 trials completed daily. As depicted in FIG. 13B, SE animals showed inter-trial improvement (detected as the difference between trials 4-5 from trials 1-2) over all training days. In contrast, no SE animals shows no further improvement following day 6 since they had already learned platform position. FIG. 13A shows that SE animals showed modest improve in escape latency over repeated days. No SE animals, however, learned the task within 6 consecutive days, with no further improvement in escape latency thereafter.

Although the foregoing invention has been described in detail for purposes of clarity of understanding, it can be obvious that certain modifications can be practiced within the scope of the appended claims. All publications, documents, accession numbers and the like cited above are hereby incorporated by reference in their entirety for all purposes to the same extent as if each were so individually denoted. If more than one version of sequence is associated with the same accession number at different times, reference to that accession number means the version associated with it at the time of filing the present application dating back to any priority application that also includes that accession number. Unless otherwise apparent from the context, any step, feature, element or embodiment can be used in combination with any other.

What is claimed is:

1. A method of treating an episode of epilepsy comprising administering an inhibitor of PSD-95 which inhibits binding of NR2B subunit of an NMDA receptor to a PDZ domain of PSD-95 in an effective regime for treatment of the episode, wherein in the effective regime for treatment of the episode the inhibitor is administered up to 4 hours after termination of an episode of epilepsy without administering the inhibitor before or during the episode wherein the inhibitor is Tat-NR2B9c (SEQ ID NO:10), F-Tat-NR2B9c (SEQ ID NO:46) or a chimeric peptide having the amino acid sequence of SEQ ID NO:8.

2. The method of claim 1, wherein the episode of epilepsy has a duration of less than 10 minutes.

3. The method of claim 2, wherein the inhibitor is Tat-NR2B9c (SEQ ID NO:10).

4. The method of claim 3, wherein the duration of the episode of epilepsy is determined using electroencephalography.

5. The method of claim 2, wherein the inhibitor is F-Tat-NR2B9c (SEQ ID NO:46).

6. The method of claim 1, wherein the episode of epilepsy comprises a continuous epileptic seizure lasting longer than 20 minutes, or comprises at least two epileptic seizures without a return to consciousness between the two seizures.

7. The method of claim 1, wherein the inhibitor is ca chimeric peptide having the amino acid sequence of SEQ ID NO:8.

8. The method of claim 1, wherein initiation and/or termination of the episode of epilepsy is determined using electroencephalography.

9. The method of claim 1, wherein the epilepsy comprises temporal lobe epilepsy.

10. The method of claim 1, wherein epileptic activity is observed in the CA1 region of the brain.

11. The method of claim 1, wherein inhibitor comprises a peptide having an amino acid sequence of SEQ ID NO:9 or SEQ ID NO:7.

12. The method of claim 1, wherein the inhibitor is administered at least one hour after termination of the episode of epilepsy.

13. The method of claim 1, wherein the inhibitor is administered at least three hours after termination of an episode of epilepsy.

* * * * *